US010369249B2

(12) United States Patent
Stewart

(10) Patent No.: US 10,369,249 B2
(45) Date of Patent: Aug. 6, 2019

(54) IN SITU SOLIDIFYING COMPLEX COACERVATES AND METHODS OF MAKING AND USING THEREOF

(71) Applicant: UNIVERSITY OF UTAH RESEARCH FOUNDATION, Salt Lake City, UT (US)

(72) Inventor: Russell J. Stewart, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/880,650

(22) Filed: Jan. 26, 2018

(65) Prior Publication Data

US 2018/0256776 A1    Sep. 13, 2018

Related U.S. Application Data

(63) Continuation of application No. 15/325,885, filed as application No. PCT/US2015/040377 on Jul. 14, 2015, now Pat. No. 9,913,927.

(60) Provisional application No. 62/024,128, filed on Jul. 14, 2014.

(51) Int. Cl.
| | |
|---|---|
| *A61L 24/10* | (2006.01) |
| *A61L 24/04* | (2006.01) |
| *A61L 24/00* | (2006.01) |
| *A61K 49/00* | (2006.01) |
| *A61L 24/02* | (2006.01) |
| *C09D 5/16* | (2006.01) |

(52) U.S. Cl.
CPC ........ *A61L 24/046* (2013.01); *A61K 49/0043* (2013.01); *A61K 49/0054* (2013.01); *A61K 49/0073* (2013.01); *A61L 24/0015* (2013.01); *A61L 24/0031* (2013.01); *A61L 24/0042* (2013.01); *A61L 24/02* (2013.01); *A61L 24/043* (2013.01); *A61L 24/10* (2013.01); *A61L 24/104* (2013.01); *C09D 5/1668* (2013.01); *A61L 2300/416* (2013.01); *A61L 2300/44* (2013.01); *A61L 2430/02* (2013.01); *A61L 2430/36* (2013.01)

(58) Field of Classification Search
None
See application file for complete search history.

(56) References Cited

U.S. PATENT DOCUMENTS

| | | | |
|---|---|---|---|
| 3,458,460 A | 7/1969 | Shepard et al. | |
| 3,947,396 A | 3/1976 | Kangas et al. | |
| 3,950,296 A | 4/1976 | Kangas et al. | |
| 4,767,463 A | 8/1988 | Brode et al. | |
| 4,913,743 A | 4/1990 | Brode et al. | |
| 5,529,914 A | 6/1996 | Hubbell et al. | |
| 6,312,725 B1 | 11/2001 | Wallace et al. | |
| 6,428,978 B1 | 8/2002 | Olsen et al. | |
| 6,497,729 B1 | 12/2002 | Moussey et al. | |
| 6,568,398 B2 | 5/2003 | Cohen | |
| 6,916,488 B1 | 7/2005 | Meier et al. | |
| 7,622,533 B2 | 11/2009 | Lee | |
| 8,283,384 B2 | 10/2012 | Stewart et al. | |
| 9,173,971 B2 | 11/2015 | Stewart | |
| 9,272,069 B2 | 3/2016 | Stewart et al. | |
| 9,421,300 B2 | 8/2016 | Stewart | |
| 2001/0016577 A1 | 8/2001 | Dobrozsi et al. | |
| 2001/0056301 A1 | 12/2001 | Goupil et al. | |
| 2002/0006886 A1 | 1/2002 | Beerse et al. | |
| 2002/0164364 A1 | 11/2002 | Quong | |
| 2002/0169476 A1 | 11/2002 | Cohen | |
| 2003/0023000 A1 | 1/2003 | Bavouzet | |
| 2004/0013738 A1 | 1/2004 | Voigt et al. | |
| 2004/0086479 A1 | 5/2004 | Grinstaff et al. | |
| 2004/0208845 A1 | 10/2004 | Michal et al. | |
| 2005/0019262 A1 | 1/2005 | Chernomorsky et al. | |
| 2005/0020734 A1 | 1/2005 | Asgarzadeh et al. | |

(Continued)

FOREIGN PATENT DOCUMENTS

| | | |
|---|---|---|
| CN | 1341032 | 3/2002 |
| CN | 1446590 | 10/2003 |

(Continued)

OTHER PUBLICATIONS

International Search Report and Written Opinion for PCT/US2015/040377 dated Oct. 13, 2015.
Treat et al., "Guanidine-Containing Methacrylamide (Co)polymers via aRAFT: Toward a Cell Penetrating Peptide Mimic," ACS Macro Letters, 2012,1:100-104.
Wang et al., "Localization of the bioadhesive precursors of the sandcastle worm, Phragmatopoma californica (Fewkes)," J. Exp. Biol., 2012, 215:351-361.

(Continued)

*Primary Examiner* — Brian Gulledge
(74) *Attorney, Agent, or Firm* — Gardner Groff Greenwald & Villanueva, PC

(57) ABSTRACT

Described herein are fluid complex coacervates that produce solid adhesives in situ. Oppositely charged polyelectrolytes were designed to form fluid adhesive complex coacervates at ionic strengths higher than the ionic strength of the application site, but an insoluble adhesive solid or gel at the application site. When the fluid, high ionic strength adhesive complex coacervates are introduced into the lower ionic strength application site, the fluid complex coacervate is converted to a an adhesive solid or gel as the salt concentration in the complex coacervate equilibrates to the application site salt concentration. In one embodiment, the fluid complex coacervates are designed to solidify in situ at physiological ionic strength and have numerous medical applications. In other aspects, the fluid complex coacervates can be used in aqueous environment for non-medical applications.

42 Claims, 10 Drawing Sheets
Specification includes a Sequence Listing.

(56) References Cited

U.S. PATENT DOCUMENTS

| | | |
|---|---|---|
| 2005/0147580 A1 | 7/2005 | Connor et al. |
| 2005/0220751 A1 | 10/2005 | Charmot et al. |
| 2005/0281883 A1 | 12/2005 | Daniloff et al. |
| 2006/0007528 A1 | 1/2006 | Cao et al. |
| 2006/0015083 A1 | 1/2006 | Munro |
| 2006/0039950 A1 | 2/2006 | Zhou et al. |
| 2006/0241242 A1 | 3/2006 | Devlin |
| 2006/0073207 A1 | 4/2006 | Masters et al. |
| 2006/0116682 A1 | 6/2006 | Longo |
| 2006/0122290 A1 | 6/2006 | Hubbell et al. |
| 2006/0156954 A1 | 7/2006 | Li et al. |
| 2006/0183848 A1 | 8/2006 | Maier et al. |
| 2006/0240064 A9 | 10/2006 | Hunter et al. |
| 2006/0275337 A1 | 12/2006 | Cohen Stuart et al. |
| 2006/0276371 A1 | 12/2006 | Schreiner et al. |
| 2007/0020469 A1 | 1/2007 | Wood et al. |
| 2007/0077276 A1 | 4/2007 | Haynie |
| 2007/0085059 A1 | 4/2007 | Mora-Guiterrez et al. |
| 2007/0191273 A1 | 8/2007 | Ambati et al. |
| 2007/0196454 A1 | 8/2007 | Stockman et al. |
| 2008/0003288 A1 | 1/2008 | Bromberg et al. |
| 2008/0075778 A1 | 3/2008 | Heller |
| 2008/0084000 A1 | 4/2008 | Forster |
| 2009/0054927 A1 | 2/2009 | Agnew |
| 2009/0162407 A1 | 6/2009 | Biggs et al. |
| 2009/0214660 A1 | 8/2009 | Vasconcellos et al. |
| 2010/0040688 A1 | 2/2010 | Elbert et al. |
| 2010/0056474 A1 | 3/2010 | Baker et al. |
| 2010/0120923 A1 | 5/2010 | Stewart et al. |
| 2010/0291169 A1 | 11/2010 | Toreki et al. |
| 2010/0305626 A1 | 12/2010 | Stewart et al. |
| 2011/0054392 A1 | 3/2011 | Nies |
| 2011/0287067 A1* | 11/2011 | Stewart ............... A61L 24/0015 424/400 |
| 2011/0288274 A1 | 11/2011 | Russell et al. |
| 2012/0177918 A1 | 7/2012 | Stewart |
| 2013/0129787 A1 | 5/2013 | Stewart |
| 2013/0189313 A1 | 7/2013 | Stewart |
| 2014/0287061 A1 | 9/2014 | Landolina |
| 2016/0250375 A1 | 9/2016 | Stewart |
| 2017/0157285 A1 | 6/2017 | Stewart |

FOREIGN PATENT DOCUMENTS

| | | |
|---|---|---|
| CN | 101405037 | 4/2009 |
| DE | 19810965 | 9/1999 |
| EP | 0632329 | 12/1997 |
| JP | 2003280056 | 12/1991 |
| JP | 2002166158 | 6/2002 |
| JP | 2009084224 | 4/2009 |
| JP | 2009084292 | 4/2009 |
| WO | 1995006056 | 3/1995 |
| WO | 2002092217 | 11/2002 |
| WO | 2002100453 | 12/2002 |
| WO | 2005019421 | 3/2005 |
| WO | 2007024972 | 3/2007 |
| WO | 2007030811 | 3/2007 |
| WO | 2009094060 | 7/2009 |
| WO | 2011011658 | 1/2011 |
| WO | 2011028967 | 3/2011 |
| WO | 2011106595 | 9/2011 |
| WO | 2011149907 | 12/2011 |
| WO | 2012065148 | 5/2012 |
| WO | 2013003400 | 1/2013 |

OTHER PUBLICATIONS

Berg et al., "The Thermal Transition of a Non-Hydroxylated Form of Collagen. Evedence for a Role for Hydroxyproline in Stabilizing the Triple-Helix of Collagen", Biochem Biophys Res Commun, 1973, vol. 52, pp. 115-12.

Hwang et al., "Expression of Functional Recombinant Mussel Adhesive Protein Mgfp-5 in *Escherichia coli*", Applied and Environmental Microbiology, 2004, vol. 70, No. 6, pp. 3352-3359.

Kamachi et al. "Synthesis of Block Polmers for Desalination Membranes. Preparation of Block Coplymers of 2-Vinylpyridine and Methacrylic Acid or Acrylic Acid", Macromolecules, 1972, vol. 5, No. 2, pp. 161-168.

Kayitmazer et al., "Mesophase Separation and Probe Dynamics in Protein-Polyelectrolyte Coacervates", Chemical Engineering Faculty Publications, 2007, vol. 3, pp. 1064-1076.

Lee et al. "Rapid Gel Formation and Adhesion in Photocurable and Biodegradable Block Copolymers with High DOPA Content", Macromolecules, 2006, vol. 39, pp. 1740-1748.

Lee et al., "Single-Molecule Mechanics of Mussel Adhesion", PNAS, 2006, vol. 103, No. 35, pp. 12999-13003.

Lee et al., "Synthesis of 3,4-dihydropxyphenylalanine (DOPA) Containing Monomers and their Co-Polymerization with PEG-Diacrylate to form Hydrogels", J. Biomater. Sci. Polymer Edn., 2004, vol. 15, No. 4, pp. 449-464.

Lim et al., "The Adhesive Properties of Coacervated Recombinant Hybrid ussel", Biomaterials, 2010, vol. 31, No. 13, pp. 3715-3722.

Liu et al., "Chemistry of Periodate Mediated Cross-Linking of 3,4-Dihydroxlphenylalanine-Containing Molecules to Proteins", J. Am. Chem. Soc., 2006, vol. 128, pp. 15228-15235.

Mo et al., "Soft tissue adhesive composed of modified gelatin and polysaccharides," J. Biomater. Sci. Polymer Edn., 2000, vol. 11, No. 4, pp. 341-351.

Polyethyleneimine:EPOMIN, website, Nippon Shokubai, 2014.

Shao et al., "A Water-Borne Adhesive Modeled after the Sandcastle Glue of P. californica," Macromolecules Bioscience, vol. 9, Issue 5, Published Online Nov. 28, 2008, pp. 464-471.

Stevens et al., "Multiscale Structure of the Underwater Adhesive of Phragmatopoma Californica: A Nanostructured Latex with a Steep Microporosity Gradient", Langmuir, 2007, vol. 23, pp. 5045-5049.

Stewart et al., "The Tube Cement of Phragmatopoma Californica: A Solid Foam", The Journal of Experimental Biology, 2004, vol. 207, No. 26, pp. 4727-4734.

Wang et al., "A novel bioadhesive protein of silk filaments spun underwater by caddisfly larvae", Adv. Mater. Res., 2009, vol. 79-82, pp. 1631-1634.

Yu et al., "Synthetic Polypeptide Mimics of Marine Adhesives", Macromolecules, 1998, vol. 31, pp. 4739-4745.

Zhao et al., "Cement Proteins of the Tube-Building Polychaete Phragmatopoma Californica", J. Biol. Chem., 2005, vol. 280, No. 52, pp. 42938-42944.

* cited by examiner

IN SITU SOLIDIFYING COMPLEX COACERVATES AND METHODS OF MAKING AND USING THEREOF

CROSS REFERENCE TO RELATED APPLICATIONS

This application is a continuation application of U.S. application Ser. No. 15/325,885, filed on Jan. 12, 2017, which is a U.S. national phase application under 35 USC 371 of international application number PCT/US2015/040377, filed Jul. 14, 2015, which claims priority to U.S. provisional application Ser. No. 62/024,128, filed Jul. 14, 2014. These applications are hereby incorporated by reference in their entireties for all of their teachings.

ACKNOWLEDGEMENTS

This invention was made with government support under R01 HD075863 awarded by the National Institutes of Health and N00014-13-1-0577 awarded by the Office of Naval Research. The government has certain rights in the invention.

CROSS REFERENCE TO SEQUENCE LISTING

Proteins described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

Numerous in situ gelling systems have been developed based on several gelling mechanisms. Reactive monomers or macromers can be chemically polymerized into hydrogels after placement in tissue. An example of this is the photoinitiated in situ polymerization of polyethyleneglycol-diacrylate (PEG-dA) macromers. Polymers with chemically reactive moieties can be chemically crosslinked in situ upon mixing with a second reactive component during or just prior to placement. An example of this approach is multi-armed PEG macromers terminated with activated ester groups. When mixed with multi-valent amines or thiols the components covalently crosslink into hydrogels. Thermosetting in situ hydrogels exploit temperature dependent transitions from viscous injectable polymer solutions to solid hydrogels. An example is ABA-type block copolymers of PEG and polypropylene oxide (PPO), which have a lower critical solution temperature (LCST) below mammalian physiological temperature. The solutions are injectable below the LCST but solidify in situ as the temperature equilibrates to the physiological temperature above the LCST. Additional in situ gelling systems depend on specific interactions between receptors and ligands, such as antibodies and antigens, on separated polymers.

Potential clinical applications of in situ gelling systems include drug delivery depots to control the release kinetics of therapeutics entrapped within the gel. Other uses include tissue augmentation for cosmetic purposes and to fill tissue voids resulting from accidental trauma or surgical resection. Systems that gel or solidify in situ are also used to block the flow of blood in blood vessels by controlled creation of localized emboli.

Current embolic agents have serious drawbacks. Cyanoacrylate (CA) adhesives are used in some cases as embolization agents. The cyanoacrylate monomers rapidly polymerize into a hard resin when they contact water in the blood vessel. CA is difficult to control, polymerizes rapidly, and can glue the end of the catheter to the blood vessels making catheter removal difficult. Onyx® is an injectable dimethylsulfoxide (DMSO) solution of ethylenevinyl alcohol. When it is injected into a watery physiological environment, the DMSO solvent diffuses out of the material causing the ethylenevinyl alcohol, which is insoluble in water, to precipitate. A drawback of Onyx® is that it can be used only in small amounts because of the toxicity of the DMSO solvent.

SUMMARY

Described herein are fluid complex coacervates that produce solid adhesives in situ. Oppositely charged polyelectrolytes were designed to form fluid adhesive complex coacervates at ionic strengths higher than the ionic strength of the application site, but an insoluble adhesive solid or gel at the application site. When the fluid, high ionic strength adhesive complex coacervates are introduced into the lower ionic strength application site, the fluid adhesive complex coacervate is converted to an adhesive solid or gel as the salt concentration in the complex coacervate equilibrates to the application site salt concentration. In one embodiment, the fluid complex coacervates are designed to solidify in situ at physiological ionic strength and have numerous medical applications. In other aspects, the fluid complex coacervates can be used in aqueous environment for non-medical applications.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
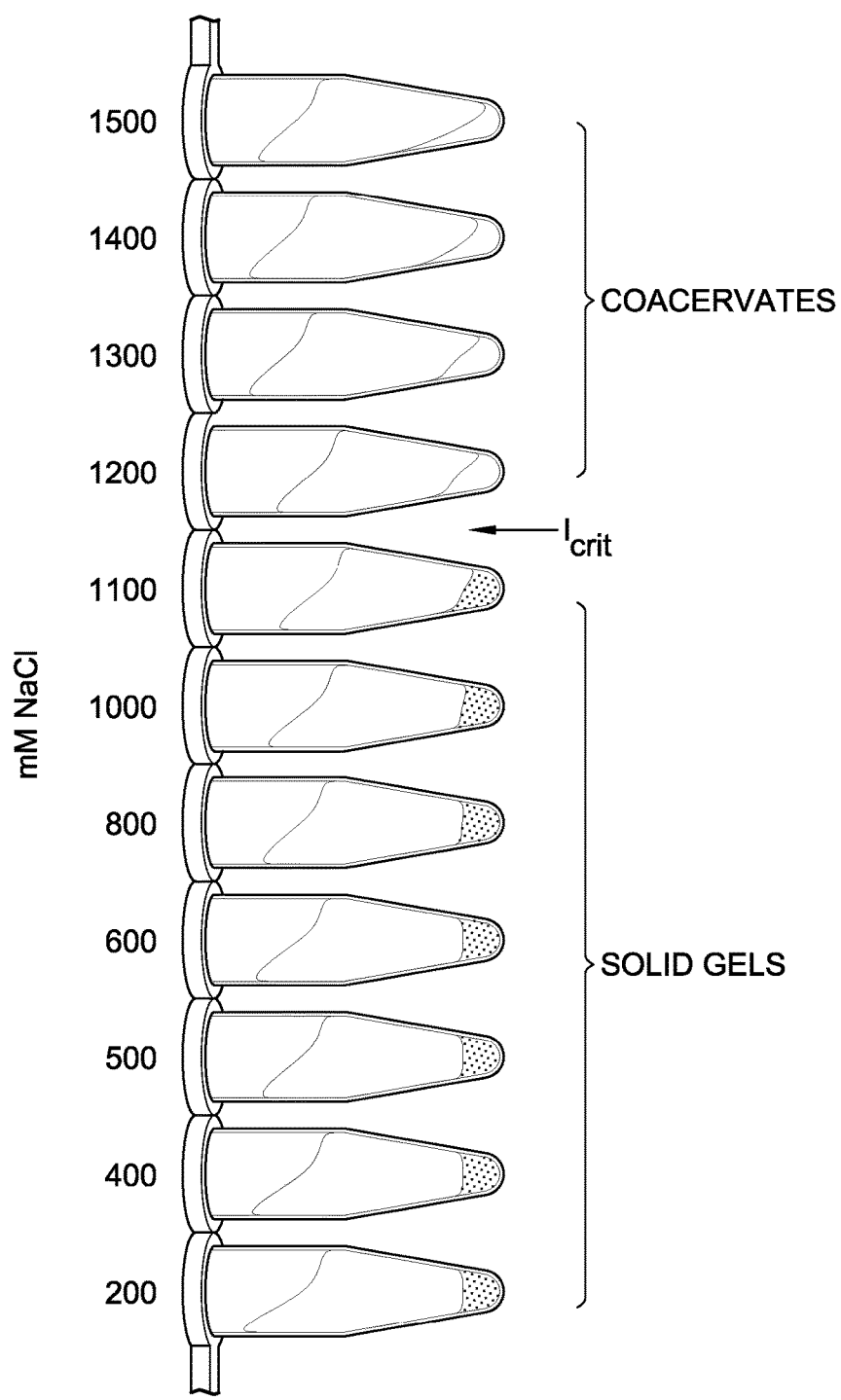
FIG. 1 shows aqueous solutions of protamine and hexametaphosphate mixed in various concentrations of NaCl. Between 1100 and 1200 mM NaCl a critical ionic strength (I) exists at which the complex coacervate becomes a solid non-flowing gel. The viscosity of the coacervate decreases with increasing I above $I_{crit}$. The stiffness of the gels increases below $I_{crit}$. The forms are interconvertible by changing the ionic strength.

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Examples of longer chain alkyl groups include, but are not limited to, a palmitate group. A "lower alkyl" group is an alkyl group containing from one to six carbon atoms.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aryl group" as used herein is any carbon-based aromatic group including, but not limited to, benzene, naphthalene, etc. The term "aryl group" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. In one aspect, the heteroaryl group is imidazole. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

The term "nucleophilic group" includes any groups capable of reacting with an activated ester. Examples include amino groups, thiols groups, hydroxyl groups, and their corresponding anions.

The term "carboxyl group" includes a carboxylic acid and the corresponding salt thereof.

The term "amino group" as used herein is represented as the formula —NHRR', where R and R' can be any organic group including alkyl, aryl, carbonyl, heterocycloalkyl, and the like, where R and R' can be separate groups or be part of a ring. For example, pyridine is a heteroaryl group where R and R' are part of the aromatic ring.

The term "treat" as used herein is defined as maintaining or reducing the symptoms of a pre-existing condition. The term "prevent" as used herein is defined as eliminating or reducing the likelihood of the occurrence of one or more symptoms of a disease or disorder. The term "reduce" as used herein is the ability of the in situ solidifying complex coacervate described herein to completely eliminate the activity or reduce the activity when compared to the same activity in the absence of the complex coacervate.

"Subject" refers to mammals including, but not limited to, humans, non-human primates, sheep, dogs, rodents (e.g., mouse, rat, etc.), guinea pigs, cats, rabbits, cows, and non-mammals including chickens, amphibians, and reptiles.

"Physiological conditions" refers to condition such as pH, temperature, etc. within the subject. For example, the physiological pH and temperature of a human is 7.2 and 37° C., respectively.

In Situ Solidifying Complex Coacervates

Polyelectrolytes with opposite net charges in aqueous solution can associate into several higher order morphologies depending on the solution conditions and charge ratios. They can form stable colloidal suspensions of polyelectrolyte complexes with net surface charges. Repulsion between like surface charges stabilize the suspension from further association. When the polyelectrolyte charge ratios are balanced, or near balance, the initial complexes can further coalesce and settle out into a dense fluid phase in which the opposite macroion charges are approximately equal. This process is referred to as complex coacervation, and the dense fluid morphology as a complex coacervate. More descriptively, the process is an associative macrophase separation of an aqueous solution of two oppositely charged polyelectrolytes into two liquid phases, a dense concentrated polyelectrolyte phase in equilibrium with a polyelectrolyte depleted phase. The aqueous coacervate phase can be dispersed into the aqueous depleted phase but quickly settles back out, like oil droplets in water. The spontaneous demixing of paired polyelectrolytes into complex coacervates occurs when attractive forces between polyelectrolyte pairs are stronger than repulsive forces. In thermodynamic terms, the net negative change in free energy that drives complex coacervation derives primarily from the gain in entropy of the small counterions released when macroions associate, which overcomes the loss of configurational entropy of the fully solvated polyelectrolytes.

Figures 10A, 10B:
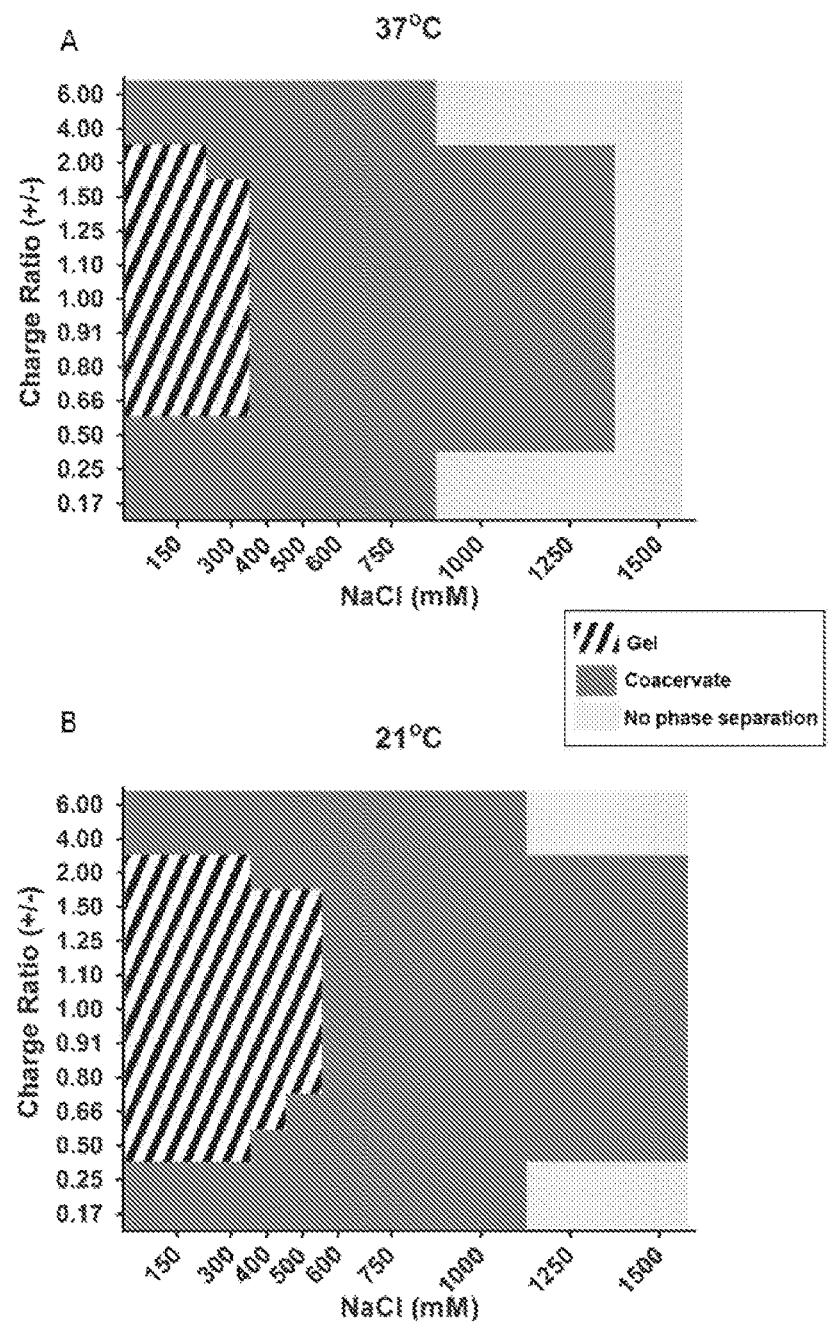
FIG. 10A shows the phase diagram of PRT/IP6 polyelectrolyte mixtures over a range of NaCl concentrations at 37° C.
FIG. 10B shows the phase diagram of PRT/IP6 polyelectrolyte mixtures over a range of NaCl concentrations at 21° C.

A non-limiting example of the different morphologies that can be produced from polyelectrolytes with opposite net charges is provided in FIGS. 1 and 10. As shown in the phase diagrams in FIGS. 10A and 10B, varying parameters such as charge ratio of the polyelectrolytes, temperature, salt concentration, and pH can result in the formation of a gel, a complex coacervate, or a clear homogeneous solution, i.e., no phase separation (FIG. 1). By mixing polyelectrolytes in a region of the phase diagram in which fluid complex coacervates form, the in situ solidifying complex coacervates described herein can be prepared in a fluid form. If the fluid form is introduced into an environment corresponding to a gel region of the phase diagram (FIG. 10), the fluid form will harden into a solid gel as the in situ solidifying complex coacervate equilibrates to the new solution conditions. The term "gel" is defined herein as non-fluid colloidal network or polymer network that is expanded throughout its whole volume by a fluid. IUPAC. Compendium of Chemical Terminology, 2nd ed. (the "Gold Book"). Compiled by A. D. McNaught and A. Wilkinson. Blackwell Scientific Publications, Oxford (1997). Conversely, the fluid complex coacervates described herein are liquids. Thus, the fluid complex coacervates described herein have a completely different morphology compared to corresponding gels produced in situ despite the fact that the polycation and polyanion in the fluid complex coacervate and the gel are identical.

The components used to produce the in situ solidifying complex coacervates described herein as well as their applications thereof are provided below.

I. Polycations

The polycation is generally composed of a polymer backbone with a plurality of cationic groups at a particular pH. The cationic groups can be pendant to the polymer backbone and/or incorporated within the polymer backbone. In certain aspects, (e.g., biomedical applications), the polycation is any biocompatible polymer possessing cationic groups or groups that can be readily converted to cationic groups by adjusting the pH. In one aspect, the polycation is a polyamine compound. The amino groups of the polyamine can be branched or part of the polymer backbone. The amino group can be a primary, secondary, or tertiary amino group that can be protonated to produce a cationic ammonium group at a selected pH. In general, the polyamine is a polymer with a large excess of positive charges relative to negative charges at the relevant pH, as reflected in its isoelectric point (pI), which is the pH at which the polymer has a net neutral charge. The number of amino groups present on the polycation ultimately determines the charge density of the polycation at a particular pH. For example, the polycation can have from 10 to 90 mole %, 10 to 80 mole %, 10 to 70 mole %, 10 to 60 mole %, 10 to 50 mole %, 10 to 40 mole %, 10 to 30 mole %, or 10 to 20 mole % amino groups. In one aspect, the polyamine has excess positive charges at a pH of about 7, with a pI significantly greater than 7. As will be discussed below, additional amino groups can be incorporated into the polymer in order to increase the pI value.

In one aspect, the amino group can be derived from a residue of lysine, histidine, or arginine attached to the polycation. For example, arginine has a guanidinyl group, where the guanidinyl group is a suitable amino group useful herein. Any anionic counterions can be used in association with the cationic polymers. The counterions should be physically and chemically compatible with the essential components of the composition and do not otherwise unduly impair product performance, stability or aesthetics. Non-limiting examples of such counterions include halides (e.g., chloride, fluoride, bromide, iodide), sulfate, methylsulfate, acetate and other monovalent carboxylic acids.

In one aspect, the polycation can be a positively-charged protein produced from a natural organism. For example, a recombinant *P. californica* protein can be used as the polycation. In one aspect, Pc1, Pc2, Pc4-Pc18 (SEQ ID NOS 1-17) can be used as the polycation. The type and number of amino acids present in the protein can vary in order to achieve the desired solution properties. For example, Pc1 is enriched with lysine (13.5 mole %) while Pc4 and Pc5 are enriched with histidine (12.6 and 11.3 mole %, respectively).

In another aspect, the polycation is a recombinant protein produced by artificial expression of a gene or a modified gene or a composite gene containing parts from several genes in a heterologous host such as, for example, bacteria, yeast, cows, goats, tobacco, and the like.

In another aspect, the polycation can be a biodegradable polyamine. The biodegradable polyamine can be a synthetic polymer or naturally-occurring polymer. The mechanism by which the polyamine can degrade will vary depending upon the polyamine that is used. In the case of natural polymers, they are biodegradable because there are enzymes that can hydrolyze the polymer chain. For example, proteases can hydrolyze natural proteins like gelatin. In the case of synthetic biodegradable polyamines, they also possess chemically labile bonds. For example, β-aminoesters have hydrolyzable ester groups. In addition to the nature of the polyamine, other considerations such as the molecular weight of the polyamine and crosslink density of the adhesive can be varied in order to modify the rate of biodegradability.

In one aspect, the biodegradable polyamine includes a polysaccharide, a protein, or a synthetic polyamine. Polysaccharides bearing one or more amino groups can be used herein. In one aspect, the polysaccharide is a natural polysaccharide such as chitosan or chemically modified chitosan. Similarly, the protein can be a synthetic or naturally-occurring compound. In another aspect, the biodegradable polyamine is a synthetic polyamine such as poly(β-aminoesters), polyester amines, poly(disulfide amines), mixed poly(ester and amide amines), and peptide crosslinked polyamines.

In the case when the polycation is a synthetic polymer, a variety of different polymers can be used; however, in certain applications such as, for example, biomedical applications, it is desirable that the polymer be biocompatible and non-toxic to cells and tissue. In one aspect, the biodegradable polyamine can be an amine-modified natural polymer. For example, the amine-modified natural polymer can be gelatin modified with one or more alkylamino groups, heteroaryl groups, or an aromatic group substituted with one or more amino groups. Examples of alkylamino groups are depicted in Formulae IV-VI

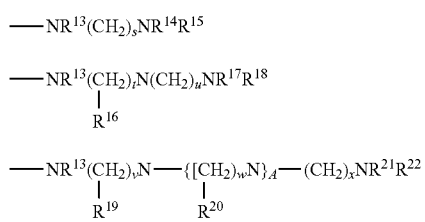

wherein $R^{13}$-$R^{22}$ are, independently, hydrogen, an alkyl group, or a nitrogen containing substituent;
s, t, u, v, w, and x are an integer from 1 to 10; and
A is an integer from 1 to 50,
where the alkylamino group is covalently attached to the natural polymer. In one aspect, if the natural polymer has a carboxyl group (e.g., acid or ester), the carboxyl group can be reacted with an alkyldiamino compound to produce an amide bond and incorporate the alkylamino group into the polymer. Thus, referring to formulae IV-VI, the amino group $NR^{13}$ is covalently attached to the carbonyl group of the natural polymer.

As shown in formula IV-VI, the number of amino groups can vary. In one aspect, the alkylamino group is —NHCH$_2$NH$_2$, —NHCH$_2$CH$_2$NH$_2$, —NHCH$_2$CH$_2$CH$_2$NH$_2$, —NHCH$_2$CH$_2$CH$_2$CH$_2$NH$_2$, —NHCH$_2$CH$_2$CH$_2$CH$_2$CH$_2$NH$_2$, —NHCH$_2$NHCH$_2$CH$_2$CH$_2$NH$_2$, —NHCH$_2$CH$_2$NHCH$_2$CH$_2$CH$_2$NH$_2$, —NHCH$_2$CH$_2$CH$_2$NHCH$_2$CH$_2$CH$_2$NHCH$_2$CH$_2$CH$_2$NH$_2$, —NHCH$_2$CH$_2$NHCH$_2$CH$_2$CH$_2$NH$_2$, —NHCH$_2$CH$_2$NHCH$_2$CH$_2$CH$_2$NHCH$_2$CH$_2$NH$_2$, or —NHCH$_2$CH$_2$NH(CH$_2$CH$_2$NH)$_d$CH$_2$CH$_2$NH$_2$, where d is from 0 to 50.

In one aspect, the amine-modified natural polymer can include an aryl group having one or more amino groups directly or indirectly attached to the aromatic group. Alternatively, the amino group can be incorporated in the aromatic ring. For example, the aromatic amino group is a pyrrole, an isopyrrole, a pyrazole, imidazole, a triazole, or an indole. In another aspect, the aromatic amino group includes the isoimidazole group present in histidine. In another aspect, the biodegradable polyamine can be gelatin modified with ethylenediamine.

In another aspect, the polycation can be a polycationic micelle or mixed micelle formed with cationic surfactants. The cationic surfactant can be mixed with nonionic surfactants to create micelles with variable charge densities. The micelles are polycationic by virtue of the hydrophobic interactions that form a polyvalent micelle. In one aspect, the micelles have a plurality of amino groups capable of reacting with the activated ester groups present on the polyanion.

Examples of nonionic surfactants include the condensation products of a higher aliphatic alcohol, such as a fatty alcohol, containing about 8 to about 20 carbon atoms, in a straight or branched chain configuration, condensed with about 3 to about 100 moles, preferably about 5 to about 40 moles, most preferably about 5 to about 20 moles of ethylene oxide. Examples of such nonionic ethoxylated fatty alcohol surfactants are the Tergitol™ 15-S series from Union Carbide and Brij™ surfactants from ICI. Tergitol™ 15-S Surfactants include $C_{11}$-$C_{15}$ secondary alcohol polyethyleneglycol ethers. Brij™ 97 surfactant is polyoxyethylene(10) oleyl ether; Brij™ 58 surfactant is polyoxyethylene (20) cetyl ether; and Brij™ 76 surfactant is polyoxyethylene (10) stearyl ether.

Another useful class of nonionic surfactants include the polyethylene oxide condensates of one mole of alkyl phenol containing from about 6 to 12 carbon atoms in a straight or branched chain configuration, with ethylene oxide. Examples of nonreactive nonionic surfactants are the Igepal™ CO and CA series from Rhone-Poulenc. Igepal™ CO surfactants include nonylphenoxy poly(ethyleneoxy) ethanols. Igepal™ CA surfactants include octylphenoxy poly(ethyleneoxy)ethanols.

Another useful class of hydrocarbon nonionic surfactants include block copolymers of ethylene oxide and propylene oxide or butylene oxide. Examples of such nonionic block copolymer surfactants are the Pluronic™ and Tetronic™ series of surfactants from BASF. Pluronic™ surfactants include ethylene oxide-propylene oxide block copolymers. Tetronic™ surfactants include ethylene oxide-propylene oxide block copolymers.

In other aspects, the nonionic surfactants include sorbitan fatty acid esters, polyoxyethylene sorbitan fatty acid esters and polyoxyethylene stearates. Examples of such fatty acid ester nonionic surfactants are the Span™, Tween™, and Myj™ surfactants from ICI. Span™ surfactants include $C_{12}$-$C_{18}$ sorbitan monoesters. Tween™ surfactants include poly(ethylene oxide) $C_{12}$-$C_{18}$ sorbitan monoesters. Myj™ surfactants include poly(ethylene oxide) stearates.

In one aspect, the nonionic surfactant can include polyoxyethylene alkyl ethers, polyoxyethylene alkyl-phenyl ethers, polyoxyethylene acyl esters, sorbitan fatty acid esters, polyoxyethylene alkylamines, polyoxyethylene alkylamides, polyoxyethylene lauryl ether, polyoxyethylene cetyl ether, polyoxyethylene stearyl ether, polyoxyethylene oleyl ether, polyoxyethylene octylphenyl ether, polyoxyethylene nonylphenyl ether, polyethylene glycol laurate, polyethylene glycol stearate, polyethylene glycol distearate, polyethylene glycol oleate, oxyethylene-oxypropylene block copolymer, sorbitan laurate, sorbitan stearate, sorbitan distearate, sorbitan oleate, sorbitan sesquioleate, sorbitan trioleate, polyoxyethylene sorbitan laurate, polyoxyethylene sorbitan stearate, polyoxyethylene sorbitan oleate, polyoxyethylene laurylamine, polyoxyethylene laurylamide, laurylamine acetate, hard beef tallow propylenediamine dioleate, ethoxylated tetramethyldecynediol, fluoroaliphatic polymeric ester, polyether-polysiloxane copolymer, and the like.

Examples of cationic surfactants useful for making cationic micelles include alkylamine salts and quaternary ammonium salts. Non-limiting examples of cationic surfactants include: the quaternary ammonium surfactants, which can have up to 26 carbon atoms include: alkoxylate quaternary ammonium (AQA) surfactants as discussed in U.S. Pat. No. 6,136,769; dimethyl hydroxyethyl quaternary ammonium as discussed in U.S. Pat. No. 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260,529 and U.S. Pat. No. 6,022,844; and amino surfactants as discussed in U.S. Pat. No. 6,221,825 and WO 00/47708, specifically amido propyldimethyl amine (APA).

In one aspect, the polycation includes a polyacrylate having one or more pendant amino groups. For example, the backbone of the polycation can be derived from the polymerization of acrylate monomers including, but not limited to, acrylates, methacrylates, acrylamides, and the like. In one aspect, the polycation backbone is derived from polyacrylamide. In other aspects, the polycation is a block co-polymer, where segments or portions of the co-polymer possess cationic groups or neutral groups depending upon the selection of the monomers used to produce the co-polymer.

In other aspects, the polycation can be a dendrimer. The dendrimer can be a branched polymer, a multi-armed polymer, a star polymer, and the like. In one aspect, the dendrimer is a polyalkylimine dendrimer, a mixed amino/ether dendrimer, a mixed amino/amide dendrimer, or an amino acid dendrimer. In another aspect, the dendrimer is poly(amidoamine), or PAMAM. In one aspect, the dendrimer has 3 to 20 arms, wherein each arm comprises an amino group.

In one aspect, the polycation is a polyamino compound. In another aspect, the polyamino compound has 10 to 90 mole % primary amino groups. In a further aspect, the polycation polymer has at least one fragment of the formula I

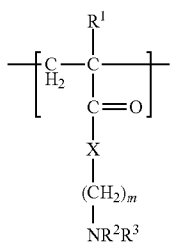

I wherein $R^1$, $R^2$, and $R^3$ are, independently, hydrogen or an alkyl group, X is oxygen or $NR^5$, where $R^5$ is hydrogen or an alkyl group, and m is from 1 to 10, or the pharmaceutically-acceptable salt thereof. In another aspect, $R^1$, $R^2$, and $R^3$ are methyl and m is 2. Referring to formula I, the polymer backbone is composed of $CH_2$—$CR^1$ units with pendant —$C(O)X(CH_2)_m NR^2R^3$ units. In one aspect, the polycation is the free radical polymerization product of a cationic primary amine monomer (3-amino-propyl methacrylate) and acrylamide, where the molecular weight is from 10 to 200 kd and possesses primary monomer concentrations from 5 to 90 mol %.

In another aspect, the polycation is a protamine. Protamines are polycationic, arginine-rich proteins that play a role in condensation of chromatin into the sperm head during spermatogenesis. As by-products of the fishing industry, commercially available protamines, purified from fish sperm, are readily available in large quantity and are relatively inexpensive. A non-limiting example of a protamine useful herein is salmine. The amino acid sequence of salmine, a protamine isolated from salmon sperm, is SEQ ID NO 18. Of the 32 amino acids, 21 are arginine (R). The guanidinyl group on the sidechain of R has a $pK_a$ of ~12.5, making salmine a densely charged polycation at physiologically relevant pH. It has a molecular mass of ~4,500 g/mol and a single negative charge at the carboxy terminus. In another aspect, the protamine is clupein.

In one aspect, the protamine can be derivatized with one or more crosslinkable groups described herein. For example, salmine can be derivatized to include one or more acrylate or methacrylate groups. An exemplary, non-limiting procedure for this embodiment is provided in the Examples. In this aspect, salmine has been derivatized on the C-terminal carboxylate with a single methacrylamide group to create a crosslinkable polycation.

In one aspect, the polycation is a natural polymer wherein one or more amine present on the natural polymer have been modified with a guanidine group. In another aspect, the polycation is a synthetic polymer containing one or more guanidinyl sidechains. For example, the polycation can be a synthetic polyguanidinyl polymer having an acrylate or methacrylate backbone and one or more guanidinyl sidechains. In another aspect, the polycation polymer has at least one fragment of the formula VIII

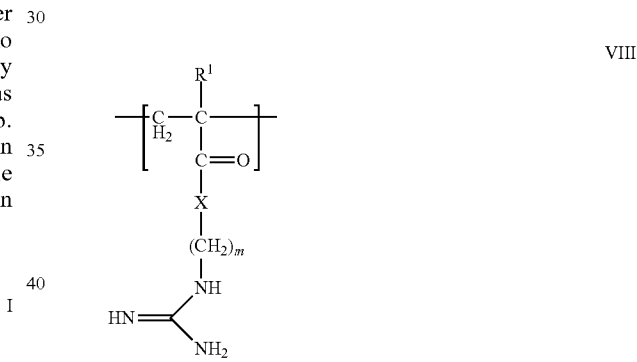

VIII wherein $R^1$ is hydrogen or an alkyl group, X is oxygen or $NR^5$, where $R^5$ is hydrogen or an alkyl group, and m is from 1 to 10, or the pharmaceutically-acceptable salt thereof. In another aspect, $R^1$, $R^2$, and $R^3$ are methyl and m is 2. Referring to formula VIII, the polymer backbone is composed of $CH_2$—$CR^1$ units with pendant —$C(O)X(CH_2)_m NC(NH)NH_2$ units. An example of a synthetic polyguanidinyl polymer useful herein is depicted in FIG. 6. An exemplary, non-limiting procedure for preparing a synthetic polyguanidinyl polymer is provided in the Examples.

Figures 6A, 6B:
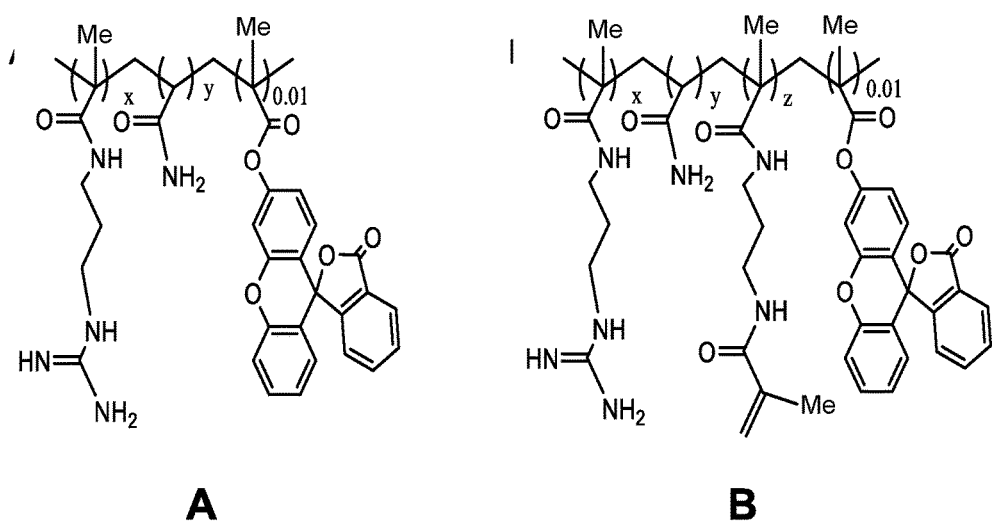
FIG. 6A shows the structure of co-polyguinidium copolymerized with a small amount of fluorescein methacrylate for visualization.
FIG. 6B shows the structure of co-polyguinidium with methacrylamide sidechains for crosslinking.

In another aspect, the synthetic polyguanidinyl polymer can be derivatized with one or more crosslinkable groups described herein. For example, one or more acrylate or methacrylate groups can be grafted onto the synthetic polyguanidinyl polymer. FIG. 6B depicts a synthetic polyguanidinyl polymer with a methacrylate sidechain. An exemplary, non-limiting procedure for this embodiment is provided in the Examples.

II. Polyanions

Similar to the polycation, the polyanion can be a synthetic polymer or naturally-occurring. Examples of naturally-occurring polyanions include glycosaminoglycans such as condroitin sulfate, heparin, heparin sulfate, dermatan sulfate, keratin sulfate, and hyaluronic acid. In other aspects, acidic proteins having a net negative charge at neutral pH or proteins with a low pI can be used as naturally-occurring polyanions described herein. The anionic groups can be pendant to the polymer backbone and/or incorporated in the polymer backbone.

When the polyanion is a synthetic polymer, it is generally any polymer possessing anionic groups or groups that can be readily converted to anionic groups by adjusting the pH. Examples of groups that can be converted to anionic groups include, but are not limited to, carboxylate, sulfonate, boronate, sulfate, borate, phosphonate, or phosphate. Any cationic counterions can be used in association with the anionic polymers if the considerations discussed above are met.

In one aspect, the polyanion is a polyphosphate. In another aspect, the polyanion is a polyphosphate compound having from 5 to 90 mole % phosphate groups. For example, the polyphosphate can be a naturally-occurring compound such as, for example, DNA, RNA, or highly phosphorylated proteins like phosvitin (an egg protein), dentin (a natural tooth phosphoprotein), casein (a phosphorylated milk protein), or bone proteins (e.g. osteopontin).

Alternatively, the polyphosphoserine can be a synthetic polypeptide made by polymerizing the amino acid serine and then chemically phosphorylating the polypeptide. In another aspect, the polyphosphoserine can be produced by the polymerization of phosphoserine. In one aspect, the polyphosphate can be produced by chemically or enzymatically phosphorylating a protein (e.g., natural serine- or threonine-rich proteins). In a further aspect, the polyphosphate can be produced by chemically phosphorylating a polyalcohol including, but not limited to, polysaccharides such as cellulose or dextran.

In another aspect, the polyphosphate can be a synthetic compound. For example, the polyphosphate can be a polymer with pendant phosphate groups attached to the polymer backbone and/or present in the polymer backbone. (e.g., a phosphodiester backbone).

In another aspect, the polyanion can be a micelle or mixed micelle formed with anionic surfactants. The anionic surfactant can be mixed with any of the nonionic surfactants described above to create micelles with variable charge densitites. The micelles are polyanionic by virtue of the hydrophobic interactions that form a polyvalent micelle.

Other useful anionic surfactants include, but are not limited to, alkali metal and (alkyl)ammonium salts of: 1) alkyl sulfates and sulfonates such as sodium dodecyl sulfate, sodium 2-ethylhexyl sulfate, and potassium dodecanesulfonate; 2) sulfates of polyethoxylated derivatives of straight or branched chain aliphatic alcohols and carboxylic acids; 3) alkylbenzene or alkylnaphthalene sulfonates and sulfates such as sodium laurylbenzene-4-sulfonate and ethoxylated and polyethoxylated alkyl and aralkyl alcohol carboxylates; 5) glycinates such as alkyl sarcosinates and alkyl glycinates; 6) sulfosuccinates including dialkyl sulfosuccinates; 7) isothionate derivatives; 8) N-acyltaurine derivatives such as sodium N methyl-N-oleyltaurate); 9) amine oxides including alkyl and alkylamidoalkyldialkylamine oxides; and 10) alkyl phosphate mono or di-esters such as ethoxylated dodecyl alcohol phosphate ester, sodium salt.

Representative commercial examples of suitable anionic sulfonate surfactants include, for example, sodium lauryl sulfate, available as TEXAPON™ L-100 from Henkel Inc., Wilmington, Del., or as POLYSTEP™ B-3 from Stepan Chemical Co, Northfield, Ill.; sodium 25 lauryl ether sulfate, available as POLYSTEP™ B-12 from Stepan Chemical Co., Northfield, Ill.; ammonium lauryl sulfate, available as STANDAPOL.™. A from Henkel Inc., Wilmington, Del.; and sodium dodecyl benzene sulfonate, available as SIPONATE™ DS-10 from Rhone-Poulenc, Inc., Cranberry, N.J., dialkyl sulfosuccinates, having the tradename AEROSOL™ OT, commercially available from Cytec Industries, West Paterson, N.J.; sodium methyl taurate (available under the trade designation NIKKOL™ CMT30 from Nikko Chemicals Co., Tokyo, Japan); secondary alkane sulfonates such as Hostapur™ SAS which is a Sodium (C14-C17) secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo(C12-C16) fatty acid available from Stepan Company under the trade designation ALPHASTE™ PC48; alkylsulfoacetates and alkylsulfosuccinates available as sodium laurylsulfoacetate (under the trade designation LANTHANOL™ LAL) and disodiumlaurethsulfosuccinate (STEPANMILD™ SL3), both from Stepan Company; alkylsulfates such as ammoniumlauryl sulfate commercially available under the trade designation STEPANOL™ AM from Stepan Company, and or dodecylbenzenesulfonic acid sold under BIO-SOFT® AS-100 from Stepan Chemical Co. In one aspect, the surfactant can be a disodium alpha olefin sulfonate, which contains a mixture of $C_{12}$ to $C_{16}$ sulfonates. In one aspect, CALSOFT™ AOS-40 manufactured by Pilot Corp. can be used herein as the surfactant. In another aspect, the surfactant is DOWFAX 2A1 or 2G manufactured by Dow Chemical, which are alkyl diphenyl oxide disulfonates.

Representative commercial examples of suitable anionic phosphate surfactants include a mixture of mono-, di- and tri-(alkyltetraglycolether)-o-phosphoric acid esters generally referred to as trilaureth-4-phosphate commercially available under the trade designation HOSTAPHAT™ 340KL from Clariant Corp., as well as PPG-5 cetyl 10 phosphate available under the trade designation CRODAPHOS™ SG from Croda Inc., Parsipanny, N.J.

Representative commercial examples of suitable anionic amine oxide surfactants those commercially available under the trade designations AMMONYX™ LO, LMDO, and CO, which are lauryldimethylamine oxide, laurylamidopropyldimethylamine oxide, and cetyl amine oxide, all from Stepan Company.

In one aspect, the polyanion includes a polyacrylate having one or more pendant phosphate groups. For example, the polyanion can be derived from the polymerization of acrylate monomers including, but not limited to, acrylates, methacrylates, and the like. In other aspects, the polyanion is a block co-polymer, where segments or portions of the co-polymer possess anionic groups and neutral groups depending upon the selection of the monomers used to produce the co-polymer.

In one aspect, the polyanion includes two or more carboxylate, sulfate, sulfonate, borate, boronate, phosphonate, or phosphate groups.

In another aspect, the polyanion is a polymer having at least one fragment having the formula XI

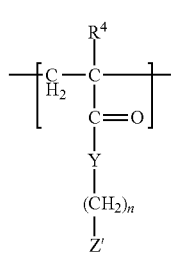

XI wherein $R^4$ is hydrogen or an alkyl group;

n is from 1 to 10;

Y is oxygen, sulfur, or $NR^{30}$, wherein $R^{30}$ is hydrogen, an alkyl group, or an aryl group;

Z' is an anionic group or a group that can be converted to an anionic group, or the pharmaceutically-acceptable salt thereof.

In one aspect, Z' in formula XI is carboxylate, sulfate, sulfonate, borate, boronate, a substituted or unsubstituted phosphate, or a phosphonate. In another aspect, Z' in formula XI is sulfate, sulfonate, borate, boronate, a substituted or unsubstituted phosphate, or a phosphonate, and n in formulae XI is 2.

In another aspect, the polyanion is an inorganic polyphosphate possessing a plurality of phosphate groups (e.g., $(NaPO_3)_n$, where n is 3 to 10). Examples of inorganic phosphates include, but are not limited to, Graham salts, hexametaphosphate salts, and triphosphate salts. The counterion of these salts can be monovalent cations such as, for example, $Na^+$, $K^+$, and $NH_4^+$.

In another aspect, the polyanion is phosphorylated sugar. The sugar can be a hexose or pentose sugar. Additionally, the sugar can be partially or fully phosphorylated. In one aspect, the phosphorylated sugar is inositol hexaphosphate.

III. Crosslinkable Groups

In certain aspects, the polycations and polyanions can contain groups that permit crosslinking between the two polymers upon curing to produce new covalent bonds. The mechanism of crosslinking can vary depending upon the selection of the crosslinking groups. In one aspect, the crosslinking groups can be electrophiles and nucleophiles. For example, the polyanion can have one or more electrophilic groups, and the polycations can have one or more nucleophilic groups capable of reacting with the electrophilic groups to produce new covalent bonds. Examples of electrophilic groups include, but are not limited to, anhydride groups, esters, ketones, lactams (e.g., maleimides and succinimides), lactones, epoxide groups, isocyanate groups, and aldehydes. Examples of nucleophilic groups are presented below. In one aspect, the polycation and polyanion can crosslink with one another via a Michael addition. For example, the polycation can have one or more nucleophilic groups such as, for example, a hydroxyl or thiol group that can react with an olefinic group present on the polyanion.

In one aspect, the crosslinking group on the polyanion comprises an olefinic group and the crosslinking group on the polycation comprises a nucleophilic group that reacts with the olefinic group to produce a new covalent bond. In another aspect, the crosslinking group on the polycation comprises an olefinic group and the crosslinking group on the polyanion comprises a nucleophilic group that reacts with the olefinic group to produce a new covalent bond.

In another aspect, the polycation and polyanion each have an actinically crosslinkable group. As used herein, "actinically crosslinkable group" in reference to curing or polymerizing means that the crosslinking between the polycation and polyanion is performed by actinic irradiation, such as, for example, UV irradiation, visible light irradiation, ionizing radiation (e.g. gamma ray or X-ray irradiation), microwave irradiation, and the like. Actinic curing methods are well-known to a person skilled in the art. The actinically crosslinkable group can be an unsaturated organic group such as, for example, an olefinic group. Examples of olefinic groups useful herein include, but are not limited to, an acrylate group, a methacrylate group, an acrylamide group, a methacrylamide group, an allyl group, a vinyl group, a vinylester group, or a styrenyl group. In another aspect, the actinically crosslinkable group can be an azido group. For example, crosslinking can occur between the polycation and polyanion via light activated crosslinking through azido groups.

Any of the polymers described above (synthetic or naturally-occurring) that can be used as the polycation and polyanion can be modified to include the actinically crosslinkable group.

In another aspect, the crosslinkable group includes a dihydroxy-substituted aromatic group capable of undergoing oxidation in the presence of an oxidant. In one aspect, the dihydroxy-substituted aromatic group is an ortho-dihydroxy aromatic group capable of being oxidized to the corresponding quinone. In another aspect, the dihydroxyl-substituted aromatic group is a dihydroxyphenol or halogenated dihydroxyphenol group such as, for example, DOPA and catechol (3,4 dihydroxyphenol). For example, in the case of DOPA, it can be oxidized to dopaquinone. Dopaquinone is capable of either reacting with a neighboring DOPA group or another nucleophilic group. In the presence of an oxidant such as oxygen or other additives including, but not limited to, peroxides, periodates (e.g., $NaIO_4$), persulfates, permanganates, dichromates, transition metal oxidants (e.g., a $Fe^{+3}$ compound, osmium tetroxide), or enzymes (e.g., catechol oxidase), the dihydroxyl-substituted aromatic group can be oxidized.

In one aspect, the polyanion is the polymerization product between two or more monomers, where one of the monomers has a dihydroxy aromatic group covalently attached to the monomer. For example, the polyanion can be the polymerization product between (1) a phosphate acrylate and/or phosphate methacrylate and (2) a second acrylate and/or second methacrylate having a dihydroxy aromatic group covalently bonded to the second acrylate or second methacrylate. In another aspect, the polyanion is the polymerization product between methacryloxyethyl phosphate and dopamine methacrylamide. In each of these polymers, an acrylate containing the pendant ortho-dihydroxyphenyl residue is polymerized with the appropriate monomers to produce the polyanion with pendant ortho-dihydroxyphenyl residues. Oxidation of ortho-dihydroxyphenyl groups results in orthoquinone groups, a reactive intermediate and can crosslink (i.e., react) with nucleophiles such as, for example, amino, hydroxyl, or thiol groups via a Michael-type addition to form a new covalent bond. For example, a lysyl group on the polycation can react with the orthoquinone residue on the polyanion to produce new covalent bonds. Other groups such as, for example, tyrosine or alkyl phenol groups can be used herein. Alkyl phenol groups can be crosslinked with peroxidase enzymes, e.g. horse radish peroxidase in the presence of $H_2O_2$. The importance of crosslinking with respect to the use of the adhesive complex coacervates described herein will be discussed below.

In certain aspects, the oxidant used above can be stabilized. For example, a compound that forms a complex with periodate that is not redox active can result in a stabilized oxidant. In other words, the periodate is stabilized in a non-oxidative form and cannot oxidize the ortho-dihydroxy-substituted aromatic group while in the complex. The complex is reversible and even if it has a very high stability constant there is a small amount of uncomplexed periodate formed. The ortho-dihydroxyl-substituted aromatic group competes with the compound for the small amount of free periodate. As the free periodate is oxidized more is released from the equilibrium complex. In one aspect, sugars possessing a cis,cis-1,2,3-triol grouping on a six-membered ring can form competitive periodate complexes. An example of a specific compound that forms stable periodate complex is 1,2-O-isopropylidene-alpha-D-glucofuranose (A. S. Perlin and E. von Rudloff, Canadian Journal of Chemistry. Volume 43 (1965)). The stabilized oxidant can control the rate of crosslinking. Not wishing to be bound by theory, the stabilized oxidant slows the rate of oxidation providing time to add the oxidant and position the substrate before the adhesive hardens irreversibly.

In other aspects, the crosslinkers present on the polycation and/or polyanion can form coordination complexes with transition metal ions. In one aspect, the polycation and/or polyanion can include groups capable of coordinating transition metal ions. Examples of coordinating sidechains are catechols, imidazoles, phosphates, carboxylic acids, and combinations. The rate of coordination and dissociation can be controlled by the selection of the coordination group, the transition metal ion, and the pH. Thus, in addition to covalent crosslinking as described above, crosslinking can occur through electrostatic, ionic, coordinative, or other non-covalent bonding. Transition metal ions such as, for example, iron, copper, vanadium, zinc, and nickel can be used herein. In one aspect, the transition metal is present in an aqueous environment at the application site.

In certain aspects, the in situ solidifying complex coacervate can also include a multivalent crosslinker. In one aspect, the multivalent crosslinker has two or more nucleophilic groups (e.g., hydroxyl, thiol, etc.) that react with crosslinkable groups (e.g., olefinic groups) present on the polycation and polyanion via a Michael addition reaction to produce a new covalent bond. In one aspect, the multivalent crosslinker is a di-thiol or tri-thiol compound.

IV. Reinforcing Components

The in situ solidifying complex coacervates described herein can optionally include a reinforcing component. The term "reinforcing component" is defined herein as any component that enhances or modifies one or more properties of the fluid complex coacervates described herein (e.g., cohesiveness, fracture toughness, elastic modulus, dimensional stability after curing, viscosity, etc.) of the in situ solidifying complex coacervate prior to or after the curing of the coacervate when compared to the same coacervate that does not include the reinforcing component. The mode in which the reinforcing component can enhance the mechanical properties of the coacervate can vary, and will depend upon the intended application of the coacervates as well as the selection of the polycation, polyanion, and reinforcing component. For example, upon curing the coacervate, the polycations and/or polyanions present in the coacervate can covalently crosslink with the reinforcing component. In other aspects, the reinforcing component can occupy a space or "phase" in the coacervate, which ultimately increases the mechanical properties of the coacervate. Examples of reinforcing components useful herein are provided below.

In one aspect, the reinforcing component is a polymerizable monomer. The polymerizable monomer entrapped in the complex coacervate can be any water soluble monomer capable of undergoing polymerization in order to produce an interpenetrating polymer network. In certain aspects, the interpenetrating network can possess nucleophilic groups (e.g., amino groups) that can react (i.e., crosslink) with the activated ester groups present on the polyanion. The selection of the polymerizable monomer can vary depending upon the application. Factors such as molecular weight can be altered to modify the solubility properties of the polymerizable monomer in water as well as the mechanical properties of the resulting coacervate, The selection of the functional group on the polymerizable monomer determines the mode of polymerization. For example, the polymerizable monomer can be a polymerizable olefinic monomer that can undergo polymerization through mechanisms such as, for example, free radical polymerization and Michael addition reactions. In one aspect, the polymerizable monomer has two or more olefinic groups. In one aspect, the monomer comprises one or two actinically crosslinkable groups as defined above.

Examples of water-soluble polymerizable monomers include, but are not limited to, hydroxyalkyl methacrylate (HEMA), hydroxyalkyl acrylate, N-vinyl pyrrolidone, N-methyl-3-methylidene-pyrrolidone, allyl alcohol, N-vinyl alkylamide, N-vinyl-N-alkylamide, acrylamides, methacrylamide, (lower alkyl)acrylamides and methacrylamides, and hydroxyl-substituted (lower alkyl)acrylamides and -methacrylamides. In one aspect, the polymerizable monomer is a diacrylate compound or dimethacrylate compound. In another aspect, the polymerizable monomer is a polyalkylene oxide glycol diacrylate or dimethacrylate. For example, the polyalkylene can be a polymer of ethylene glycol, propylene glycol, or block copolymers thereof. In one aspect, the polymerizable monomer is polyethylene glycol diacrylate or polyethylene glycol dimethacrylate. In one aspect, the polyethylene glycol diacrylate or polyethylene glycol dimethacrylate has a $M_n$ of 200 to 2,000, 400 to 1,500, 500 to 1,000, 500 to 750, or 500 to 600.

In certain aspects, the interpenetrating polymer network is biodegradable and biocompatible for medical applications. Thus, the polymerizable monomer is selected such that a biodegradable and biocompatible interpenetrating polymer network is produced upon polymerization. For example, the polymerizable monomer can possess cleavable ester linkages. In one aspect, the polymerizable monomer is hydroxypropyl methacrylate (HPMA), which will produce a biocompatible interpenetrating network. In other aspects, biodegradable crosslinkers can be used to polymerize biocompatible water soluble monomers such as, for example, alkyl methacrylamides. The crosslinker could be enzymatically degradable, like a peptide, or chemically degradable by having an ester or disulfide linkage. In another aspect, the reinforcing component can be a natural or synthetic fiber.

In other aspects, the reinforcing component can be a water-insoluble filler. The filler can have a variety of different sizes and shapes, ranging from particles (micro and nano) to fibrous materials. The selection of the filler can vary depending upon the application of the in situ solidifying complex coacervate.

The fillers useful herein can be composed of organic and/or inorganic materials. In one aspect, the nanostructures can be composed of organic materials like carbon or inorganic materials including, but not limited to, boron, molybdenum, tungsten, silicon, titanium, copper, bismuth, tungsten carbide, aluminum oxide, titanium dioxide, molybdenum disulphide, silicon carbide, titanium diboride, boron nitride, dysprosium oxide, iron (III) oxide-hydroxide, iron oxide, manganese oxide, titanium dioxide, boron carbide, aluminum nitride, or any combination thereof.

In certain aspects, the fillers can be functionalized in order to react (i.e., crosslink) with the polycation and/or polyanion. For example, the filler can be functionalized with amino groups or activated ester groups. In other aspects, it is desirable to use two or more different types of fillers. For example, a carbon nanostructure can be used in combination with one or more inorganic nanostructures.

In one aspect, the filler comprises a metal oxide, a ceramic particle, or a water insoluble inorganic salt. Examples of fillers useful herein include those manufactured by SkySpring Nanomaterials, Inc., which is listed below.

Metals and Non-Metal Elements
Ag, 99.95%, 100 nm
Ag, 99.95%, 20-30 nm

Ag, 99.95%, 20-30 nm, PVP coated
Ag, 99.9%, 50-60 nm
Ag, 99.99%, 30-50 nm, oleic acid coated
Ag, 99.99%, 15 nm, 10 wt %, self-dispersible
Ag, 99.99%, 15 nm, 25 wt %, self-dispersible
Al, 99.9%, 18 nm
Al, 99.9%, 40-60 nm
Al, 99.9%, 60-80 nm
Al, 99.9%, 40-60 nm, low oxygen
Au, 99.9%, 100 nm
Au, 99.99%, 15 nm, 10 wt %, self-dispersible
B, 99.9999%
B, 99.999%
B, 99.99%
B, 99.9%
B, 99.9%, 80 nm
Diamond, 95%, 3-4 nm
Diamond, 93%, 3-4 nm
Diamond, 55-75%, 4-15 nm
Graphite, 93%, 3-4 nm
Super Activated Carbon, 100 nm
Co, 99.8%, 25-30 nm
Cr, 99.9%, 60-80 nm
Cu, 99.5%, 300 nm
Cu, 99.5%, 500 nm
Cu, 99.9%, 25 nm
Cu, 99.9%, 40-60 nm
Cu, 99.9%, 60-80 nm
Cu, 5-7 nm, dispersion, oil soluble
Fe, 99.9%, 20 nm
Fe, 99.9%, 40-60 nm
Fe, 99.9%, 60-80 nm
Carbonyl-Fe, micro-sized
Mo, 99.9%, 60-80 nm
Mo, 99.9%, 0.5-0.8 nm
Ni, 99.9%, 500 nm (adjustable)
Ni, 99.9%, 20 nm
Ni coated with carbon, 99.9%, 20 nm
Ni, 99.9%, 40-60 nm
Ni, 99.9%, 60-80 nm
Carbonyl-Ni, 2-3 µm
Carbonyl-Ni, 4-7 µm
Carbonyl-Ni—Al (Ni Shell, Al Core)
Carbonyl-Ni—Fe Alloy
Pt, 99.95%, 5 nm, 10 wt %, self-dispersible
Si, Cubic, 99%, 50 nm
Si, Polycrystalline, 99.99995%, lumps
Sn, 99.9%, <100 nm
Ta, 99.9%, 60-80 nm
Ti, 99.9%, 40-60 nm
Ti, 99.9%, 60-80 nm
W, 99.9%, 40-60 nm
W, 99.9%, 80-100 nm
Zn, 99.9%, 40-60 nm
Zn, 99.9%, 80-100 nm
Metal Oxides
AlOOH, 10-20 nm, 99.99%
$Al_2O_3$ alpha, 98+%, 40 nm
$Al_2O_3$ alpha, 99.999%, 0.5-10 µm
$Al_2O_3$ alpha, 99.99%, 50 nm
$Al_2O_3$ alpha, 99.99%, 0.3-0.8 µm
$Al_2O_3$ alpha, 99.99%, 0.8-1.5 µm
$Al_2O_3$ alpha, 99.99%, 1.5-3.5 µm
$Al_2O_3$ alpha, 99.99%, 3.5-15 µm
$Al_2O_3$ gamma, 99.99%, 5 nm
$Al_2O_3$ gamma, 99.99%, 20 nm
$Al_2O_3$ gamma, 99.99%, 0.4-1.5 µm
$Al_2O_3$ gamma, 99.99%, 3-10 µm
$Al_2O_3$ gamma, Extrudate
$Al_2O_3$ gamma, Extrudate
$Al(OH)_3$, 99.99%, 30-100 nm
$Al(OH)_3$, 99.99%, 2-10 µm
Aluminium Iso-Propoxide (AIP), $C_9H_{21}O_3Al$, 99.9%
AlN, 99%, 40 nm
BaTiO3, 99.9%, 100 nm
$BBr_3$, 99.9%
$B_2O_3$, 99.5%, 80 nm
BN, 99.99%, 3-4 µm
BN, 99.9%, 3-4 µm
$B_4C$, 99%, 50 nm
$Bi_2O_3$, 99.9%, <200 nm
$CaCO_3$, 97.5%, 15-40 nm
$CaCO_3$, 15-40 nm
$Ca_3(PO_4)_2$, 20-40 nm
$Ca_{10}(PO_4)_6(OH)_2$, 98.5%, 40 nm
$CeO_2$, 99.9%, 10-30 nm
CoO, <100 nm
$Co_2O_3$, <100 nm
$Co_3O_4$, 50 nm
CuO, 99+%, 40 nm
$Er_2O_3$, 99.9%, 40-50 nm
$Fe_2O_3$ alpha, 99%, 20-40 nm
$Fe_2O_3$ gamma, 99%, 20-40 nm
$Fe_3O_4$, 98+%, 20-30 nm
$Fe_3O_4$, 98+%, 10-20 nm
$Gd_2O_3$, 99.9%<100 nm
$HfO_2$, 99.9%, 100 nm
$In_2O_3:SnO_2$=90:10, 20-70 nm
$In_2O_3$, 99.99%, 20-70 nm
$In(OH)_3$, 99.99%, 20-70 nm
$LaB_6$, 99.0%, 50-80 nm
$La_2O_3$, 99.99%, 100 nm
$LiFePO_4$, 40 nm
MgO, 99.9%, 10-30 nm
MgO, 99%, 20 nm
MgO, 99.9%, 10-30 nm
$Mg(OH)_2$, 99.8%, 50 nm
$Mn_2O_3$, 98+%, 40-60 nm
$MoCl_5$, 99.0%
$Nd_2O_3$, 99.9%, <100 nm
NiO, <100 nm
$Ni_2O_3$, <100 nm
$Sb_2O_3$, 99.9%, 150 nm
$SiO_2$, 99.9%, 20-60 nm
$SiO_2$, 99%, 10-30 nm, treated with Silane Coupling Agents
$SiO_2$, 99%, 10-30 nm, treated with Hexamethyldisilazane
$SiO_2$, 99%, 10-30 nm, treated with Titanium Ester
$SiO_2$, 99%, 10-30 nm, treated with Silanes
$SiO_2$, 10-20 nm, modified with amino group, dispersible
$SiO_2$, 10-20 nm, modified with epoxy group, dispersible
$SiO_2$, 10-20 nm, modified with double bond, dispersible
$SiO_2$, 10-20 nm, surface modified with double layer, dispersible
$SiO_2$, 10-20 nm, surface modified, super-hydrophobic & oleophilic, dispersible
$SiO_2$, 99.8%, 5-15 nm, surface modified, hydrophobic & oleophilic, dispersible
$SiO_2$, 99.8%, 10-25 nm, surface modified, super-hydrophobic, dispersible
SiC, beta, 99%, 40 nm
SiC, beta, whisker, 99.9%
$Si_3N_4$, amorphous, 99%, 20 nm
$Si_3N_4$ alpha, 97.5-99%, fiber, 100 nm×800 nm
$SnO_2$, 99.9%, 50-70 nm ATO, $SnO_2:Sb_2O_3$=90:10, 40 nm
$TiO_2$ anatase, 99.5%, 5-10 nm
$TiO_2$ Rutile, 99.5%, 10-30 nm
$TiO_2$ Rutile, 99%, 20-40 nm, coated with $SiO_2$, highly hydrophobic
$TiO_2$ Rutile, 99%, 20-40 nm, coated with $SiO_2/Al_2O_3$
$TiO_2$ Rutile, 99%, 20-40 nm, coated with $Al_2O_3$, hydrophilic
$TiO_2$ Rutile, 99%, 20-40 nm, coated with $SiO_2/Al_2O_3$/ Stearic Acid
$TiO_2$ Rutile, 99%, 20-40 nm, coated with Silicone Oil, hydrophobic
TiC, 99%, 40 nm
TiN, 97+%, 20 nm
$WO_3$, 99.5%, <100 nm
$WS_2$, 99.9%, 0.8 μm
$WCl_6$, 99.0%
$Y_2O_3$, 99.995%, 30-50 nm
ZnO, 99.8%, 10-30 nm
ZnO, 99%, 10-30 nm, treated with silane coupling agents
ZnO, 99%, 10-30 nm, treated with stearic acid
ZnO, 99%, 10-30 nm, treated with silicone oil
ZnO, 99.8%, 200 nm
$ZrO_2$, 99.9%, 100 nm
$ZrO_2$, 99.9%, 20-30 nm
$ZrO_2$-3Y, 99.9%, 0.3-0.5 um
$ZrO_2$-3Y, 25 nm
$ZrO_2$-5Y, 20-30 nm
$ZrO_2$-8Y, 99.9%, 0.3-0.5 μm
$ZrO_2$-8Y, 20 nm
ZrC, 97+%, 60 nm In one aspect, the filler is nanosilica. Nanosilica is commercially available from multiple sources in a broad size range. For example, aqueous Nexsil colloidal silica is available in diameters from 6-85 nm from Nyacol Nanotechnologies, Inc. Amino-modified nanosilica is also commercially available, from Sigma Aldrich for example, but in a narrower range of diameters than unmodified silica. Nanosilica does not contribute to the opacity of the coacervate, which is an important attribute of the adhesives and glues produced therefrom.

In another aspect, the filler can be composed of calcium phosphate. In one aspect, the filler can be hydroxyapatite, which has the formula $Ca_5(PO_4)_3OH$. In another aspect, the filler can be a substituted hydroxyapatite. A substituted hydroxyapatite is hydroxyapatite with one or more atoms substituted with another atom. The substituted hydroxyapatite is depicted by the formula $M_5X_3Y$, where M is Ca, Mg, Na; X is $PO_4$ or $CO_3$; and Y is OH, F, Cl, or $CO_3$. Minor impurities in the hydroxyapatite structure may also be present from the following ions: Zn, Sr, Al, Pb, Ba. In another aspect, the calcium phosphate comprises a calcium orthophosphate. Examples of calcium orthophosphates include, but are not limited to, monocalcium phosphate anhydrate, monocalcium phosphate monohydrate, dicalcium phosphate dihydrate, dicalcium phosphate anhydrous, octacalcium phosphate, beta tricalcium phosphate, alpha tricalcium phosphate, super alpha tricalcium phosphate, tetracalcium phosphate, amorphous tricalcium phosphate, or any combination thereof. In other aspects, the calcium phosphate can also include calcium-deficient hydroxyapatite, which can preferentially adsorb bone matrix proteins.

In certain aspects, the filler can be functionalized with one or more amino or activated ester groups. In this aspect, the filler can be covalently attached to the polycation or polyanion. For example, aminated silica can be reacted with the polyanion possessing activated ester groups to form new covalent bonds.

In other aspects, the filler can be modified to produce charged groups such that the filler can form electrostatic bonds with the coacervates. For example, aminated silica can be added to a solution and the pH adjusted so that the amino groups are protonated and available for electrostatic bonding.

In one aspect, the reinforcing component can be micelles or liposomes. In general, the micelles and liposomes used in this aspect are different from the micelles or liposomes used as polycations and polyanions for preparing the coacervate. The micelles and liposomes can be prepared from the nonionic, cationic, or anionic surfactants described above. The charge of the micelles and liposomes can vary depending upon the selection of the polycation or polyanion as well as the intended use of the coacervate. In one aspect, the micelles and liposomes can be used to solubilize hydrophobic compounds such pharmaceutical compounds. Thus, in addition to be used as adhesives, the adhesive complex coacervates described herein can be effective as a bioactive delivery device.

V. Initiators

In certain aspects, the in situ solidifying complex coacervate also includes one or more initiators entrapped in the coacervate. Examples of initiators useful herein include a thermal initiator, a chemical initiator, or a photoinitiator to promote crosslinking amongst the different components in the complex coacervate composition.

Examples of photoinitiators include, but are not limited to a phosphine oxide, peroxides, peracids, azide compounds, α-hydroxyketones, or α-aminoketones. In one aspect, the photoinitiator includes, but is not limited to, camphorquinone, benzoin methyl ether, 1-hydroxycyclohexylphenyl ketone, or Darocure® or Irgacure® types, for example Darocure® 1173 or Irgacure® 2959. The photoinitiators disclosed in European Patent No. 0632329, which are incorporated by reference, can be used herein. In other aspects, the photoinitiator is a water-soluble photoinitiator including, but not limited to, riboflavin, eosin, eosin y, and rose Bengal.

In one aspect, the initiator has a positively charged functional group. Examples include 2,2'-azobis[2-(5-methyl-2-imidazolin-2-yl)propane]-dihydrochloride; 2,2'-azobis[2-(2-imidazolin-2-yl) propane]dihydrochloride; 2,2'-azobis[2-(2-imidazo-lin-2-yl)propane]disulfate dehydrate; 2,2'-azobis(2-methylpropionamidine)dihydrochloride; 2,2'-azobis[2-(3,4,5,6-tetrahydropyrimidin-2-yl)propane]dihydrochloride; azobis{2-[1-(2-hydroxyethyl)-2-imidazolin-2-yl]propane}dihydrochloride; 2,2'-azobis(1-imino-1-pyrrolidino-2-ethylpropane)dihydrochloride and combinations thereof.

In another aspect, the initiator is an oil soluble initiator. In one aspect, the oil soluble initiator includes organic peroxides or azo compounds.

Examples of organic peroxides include ketone peroxides, peroxyketals, hydroperoxides, dialkyl peroxides, diacyl peroxides, peroxydicarbonates, peroxyesters, and the like. Some specific non-limiting examples of organic peroxides that can be used as the oil soluble initiator include: lauroyl peroxide, 1,1-bis(t-hexylperoxy)-3,3,5-trimethylcyclohexane, 1,1-bis(t-butylperoxy)-3,3,5-trimethylcyclohexane, t-butylperoxylaurate, t-butylperoxyisopropylmonocarbonate, t-butylperoxy-2-ethylhexylcarbonate, di-t-butylperoxy-hexahydro-terephthalate, dicumyl peroxide, 2,5-dimethyl-2, 5-di(t-butylperoxy)hexane, di-t-butyl peroxide, t-butylperoxy-2-ethylhexanoate, bis(4-t-butylcyclohexyl) peroxydi-carbonate, t-amylperoxy-3,5,5-trimethylhexanoate, 1,1-di(t-amylperoxy)-3,3,5-trimethylcyclohexane, benzoyl-peroxide, t-butylperoxyacetate, and the like.

Some specific non-limiting examples of azo compounds that can be used as the oil soluble initiator include: 2,2'-azobis-isobutyronitrile, 2,2'-azobis-2,4-dimethylvaleronitrile, 1,1'-azobis-1-cyclohexane-carbonitrile, dimethyl-2,2'-azobisisobutyrate, 1,1'-azobis-(1-acetoxy-1-phenylethane), 4,4'-azobis(4-cyanopentanoic acid) and its soluble salts (e.g., sodium, potassium), and the like.

In one aspect, the initiator is a water-soluble initiator including, but not limited to, potassium persulfate, ammonium persulfate, sodium persulfate, and mixtures thereof. In another aspect, the initiator is an oxidation-reduction initiator such as the reaction product of the above-mentioned persulfates and reducing agents such as sodium metabisulfite and sodium bisulfite; and 4,4'-azobis(4-cyanopentanoic acid) and its soluble salts (e.g., sodium, potassium).

In certain aspects, multiple initiators can be used to broaden the absorption profile of the initiator system in order to increase the initiation rate. For example, two different photoinitiators can be employed that are activated by different wavelengths of light. In another aspect, a co-initiator can be used in combination with any of the initiators described herein. In one aspect, the co-initiator is 2-(diethylamino)ethyl acrylate, 2-(dimethylamino)ethyl acrylate, 2-(dimethylamino)ethyl benzoate, 2-(dimethylamino)ethyl methacrylate, 2-ethylhexyl 4-(dimethylamino)benzoate, 3-(dimethylamino)propyl acrylate, 4,4'-bis(diethylamino) benzophenone, or 4-(diethylamino)benzophenone.

In certain aspects, the initiator and/or co-initiator are covalently attached to the polycation and/or polyanion. For example, the initiator and/or co-initiator can be copolymerized with monomers used to make the polycation and/or polyanion. In one aspect, the initiators and co-initiators possess polymerizable olefinic groups such as acrylate and methacrylate groups (e.g., see examples of co-initiators above) that can be copolymerized with monomers described above used to make the polycation and polyanion. In another aspect, the initiators can be chemically grafted onto the backbone of the polycation and polyanion. Thus, in these aspects, the photoinitiator and/or co-initiator are covalently attached to the polymer and pendant to the polymer backbone. This approach will simply formulation and possibly enhance storage and stability.

In other aspects, the initiator and/or co-initiator are electrostatically associated into the fluid complex coacervate.

VI. Multivalent Cations

The in situ solidifying complex coacervates can optionally contain one or more multivalent cations (i.e., cations having a charge of +2 or greater). In one aspect, the multivalent cation can be a divalent cation composed of one or more alkaline earth metals. For example, the divalent cation can be a mixture of $Ca^{+2}$ and $Mg^{+2}$. In other aspects, transition metal ions with a charge of +2 or greater can be used as the multivalent cation. The concentration of the multivalent cations can determine the rate and extent of coacervate formation. Not wishing to be bound by theory, weak cohesive forces between particles in the fluid may be mediated by multivalent cations bridging excess negative surface charges. The amount of multivalent cation used herein can vary. In one aspect, the amount is based upon the number of anionic groups and cationic groups present in the polyanion and polycation.

Preparation of In Situ Solidifying Complex Coacervates

The synthesis of the in situ solidifying complex coacervates described herein can be performed using a number of techniques and procedures. Exemplary techniques for producing the coacervates are provided in the Examples. In one aspect, the polycation and polyanion are mixed as dilute solutions. Upon mixing, when the polycation and polyanion associate they condense into a fluid/liquid phase at the bottom of a mixing chamber (e.g., a tube) to produce a condensed phase. The condensed phase (i.e., fluid complex coacervate) is separated and used as the in situ solidifying complex coacervate.

In one aspect, an aqueous solution of polycation is mixed with an aqueous solution of polyanion such that the positive/negative charge ratio of the polycation to the polyanion is from 4 to 0.25, 3 to 0.25, 2 to 0.25, 1.5 to 0.5, 1.10 to 0.95, 1 to 1. Depending upon the number of charged groups on the polycation and polyanion, the amount of polycation and polyanion can be varied in order to achieve specific positive/negative charge ratios. The in situ solidifying complex coacervate contains water, wherein the amount of water is from 20% to 80% by weight of the composition.

The pH of the solution containing the polycation, polyanion, and the monovalent salt can vary in order to optimize complex coacervate formation. In one aspect, the pH of the composition containing the in situ solidifying complex coacervate is from 6 to 9, 6.5 to 8.5, 7 to 8, or 7 to 7.5. In another aspect, the pH of the composition is 7.2 (i.e., physiological pH).

The amount of the monovalent salt that is present in the in situ solidifying complex coacervate can vary depending upon the concentration of the monovalent salt in the environment at which the in situ solidifying complex coacervate is introduced. This is demonstrated in the Examples and FIGS. 10A and 10B. In general, the concentration of the monovalent salt in the complex coacervate is greater than the concentration of the monovalent salt in the environment. For example, the concentration of Na and KCl under physiological conditions is about 150 mM. Therefore, if the in situ solidifying complex coacervate is to be administered to a human subject, the concentration of the monovalent salt present in the in situ solidifying complex coacervate would be greater than 150 mM. In one aspect, the monovalent salt that is present in the in situ solidifying complex coacervate is at a concentration from 0.5 M to 2.0 M. In another aspect, the concentration of the monovalent salt is 0.5 to 1.8, 0.5 to 1.6, 0.5 to 1.4, or 0.5 to 1.2. In another aspect, the concentration of the monovalent salt in the complex coacervate is 1.5 to 2, 1.5 to 3, 1.5 to 4, 1.5 to 5, 1.5 to 6, 1.5 to 7, 1.5 to 8, 1.5 to 9 or 1.5 to 10 times greater than the concentration of the monovalent salt in the aqueous environment.

In one aspect, the monovalent salt can be sodium chloride or potassium chloride or a mixture. In other aspects, the in situ solidifying complex coacervate can be formulated in hypertonic saline solutions that can be used for parenteral or intravenous administration or by injection to a subject. In one aspect, the in situ solidifying complex coacervate can be formulated in Ringer's dextrose, dextrose and sodium chloride, lactated Ringer's, or other buffered saline solutions that can be safely administered to a subject, wherein the saline concentration has been adjusted so that it is greater than saline concentration at physiological conditions.

Kits

The polycations and polyanions described herein can be stored as dry powders for extended periods of time. This feature is very useful for preparing the coacervates and ultimately the adhesives when desired. Thus, described herein are kits for making the in situ solidifying complex coacervates and adhesives described herein. In one aspect, the kit comprises (1) at least one polyanion, (2) at least one polycation, wherein the positive/negative charge ratio of the polycation to the polyanion is from 0.25 to 4, and (3) an aqueous solution comprising a monovalent salt at a concentration from 0.5 M to 2.0 M. The kits can also include additional components as described herein (e.g., reinforcing components, initiators, bioactive agents, contrast agents, etc.).

When stored as dried powders, water can be added to the polycation and/or polyanion to produce the coacervate. In one aspect, prior to lyophilizing the polycation and polyanion in order to produce a dry powder, the pH of the polycation and polyanion can be adjusted such that when they are admixed in water the desired pH is produced without the addition of acid or base. For example, excess base can be present in the polycation powder which upon addition of water adjusts the pH accordingly.

In another aspect, the in situ solidifying complex coacervate can be loaded in a syringe for future. Due to the stability of the in situ solidifying complex coacervate, a sterilized solution of the complex coacervate can be stored in the syringe for extended periods of time and used as needed.

Applications of the In Situ Solidifying Complex Coacervates

The in situ solidifying complex coacervates and adhesives described herein have numerous benefits and applications where it is desirable to produce adhesives and coatings in an aqueous environment. As discussed above, the in situ solidifying complex coacervates are fluids with low viscosity and are readily injectable via a narrow gauge device, syringe, catheter, needle, cannula, or tubing. The in situ solidifying complex coacervates are water-borne eliminating the need for potentially toxic solvents.

The in situ solidifying complex coacervates described herein are fluids at ionic strengths higher than the ionic strength of the application site, but insoluble ionic hydrogels at the ionic strength of the application site. When the fluid, high ionic strength complex coacervates are introduced into a lower ionic strength application site, the complex coacervates forms a solid or gel in situ at the application site as the salt concentration in the complex coacervate equilibrates to the application site salt concentration. The solid or gel that is subsequently produced is a non-fluid, water insoluble material.

The ionic concentration at the application site can vary depending upon the ionic concentration of the in situ solidifying complex coacervate. In one aspect, the application site has one or more monovalent salts, where the concentration of the monovalent salts is less than 500 mM, or from 150 mM to less than 500 mM. In another aspect, the ionic concentration of the monovalent salt at the application site is from 150 mM to 600 mM and the concentration of the monovalent salt of the complex coacervate composition is greater than 600 mM to 2 M.

The in situ solidifying complex coacervates can form solids or gels in situ under physiological conditions. The physiological ionic strength is approximately 300 mOsm/L. Thus, when in situ solidifying complex coacervates having an ionic strength greater than 300 mOsm/L are introduced to a subject (e.g., injected into a mammal), the fluid complex coacervate is converted to an adhesive solid or gel at the site of application. Thus, the in situ solidifying complex coacervates described herein have numerous medical and biological applications, which are described in detail below.

In one aspect, the in situ solidifying complex coacervates can include one or more contrast agents. Upon administration of the in situ solidifying complex coacervates to the subject, the physician can monitor precisely the position of the adhesive gel or solid that is produced in situ. Contrast agents known in the art can be used herein. In one aspect, the contrast agent can be admixed with the polycation and polyanion. For example, metal particles such as tantalum powder or gold can be used. Alternatively soluble iodine complexes can be used as the contrast agent. The contrast agent can be detected using techniques known in the art including X-ray, NMR imaging, ultrasound, and fluoroscopes.

In other aspect, a visualization agent can be used to visibly detect the position of the complex coacervate. An example of this is depicted in FIG. 6B, where fluorescein is covalently bonded to a synthetic polyguanidinyl polymer (i.e., a polycation). Thus, in one aspect, polymerizable monomers with a contrast or visualization agent covalently bonded to it can be polymerized with other monomers to produce polycations and polyanions useful herein medical and biological applications.

In one aspect, the in situ solidifying complex coacervates and adhesive solids and gels produced therefrom can be used to reduce or inhibit blood flow in a blood vessel of a subject. In this aspect, the adhesive solid or gel produced from the fluid complex coacervate creates an artificial embolus within the vessel. Thus, the fluid complex coacervates described herein can be used as synthetic embolic agents. In this aspect, the in situ solidifying complex coacervate is injected into the vessel followed by formation of the adhesive solid or gel in order to partially or completely block the vessel. This method has numerous applications including hemostasis or the creation of an artificial embolism to inhibit blood flow to a tumor, aneurysm, varicose vein, an arteriovenous malformation, an open or bleeding wound, or other vascular defects.

As discussed above, the fluid complex coacervates can be used as synthetic embolic agents. However, in other aspects, the fluid complex coacervate described herein can include one or more additional embolic agents. Embolic agents commercially-available are microparticles used for embolization of blood vessels. The size and shape of the microparticles can vary. In one aspect, the microparticles can be composed of polymeric materials. An example of this is Bearin™ nsPVA particles manufactured by Merit Medical Systems, Inc., which are composed of polyvinyl alcohol ranging is size from 45 µm to 1,180 µm. In another aspect, the embolic agent can be a microsphere composed of a polymeric material. Examples of such embolic agents include Embosphere® Microspheres, which are made from trisacryl cross linked with gelatin ranging is size from 40 µm to 1,200 µm; HepaSphere™ Microspheres (spherical, hydrophilic microspheres made from vinyl acetate and methyl acrylate) ranging is size from 30 µm to 200 µm; and QuadraSphere® Microspheres (spherical, hydrophilic microspheres made from vinyl acetate and methyl acrylate) ranging is size from 30 µm to 200 µm, all of which are manufactured by Merit Medical Systems, Inc. In another aspect, the microsphere can be impregnated with one or more metals that can be used as a contrast agent. An example of this is EmboGold® Microspheres manufactured by Merit Medical Systems, Inc., which are made from trisacryl cross linked with gelatin impregnated with 2% elemental gold ranging is size from 40 µm to 1,200 µm.

In another aspect, the fluid complex coacervate includes a contrast agent for visualizing the location of the solid or gel that is produced in the subject from the fluid complex coacervate. The contrast agents and methods for visualizing discussed above can be used in this embodiment. In one aspect, the contrast agent can be tantalum particles having a particle size from 0.5 µm to 50 µm, 1 µm to 25 µm, 1 µm to 10 µm, or 1 µm to 5 µm. In another aspect, contrast agent is tantalum particles in the amount of 10% to 60%, 20% to 50%, or 20% to 40%.

In the case of embolic applications, the addition of components such as contrast agents or embolic agents can affect the viscosity of the fluid complex coacervate and administration to a subject. For example, a fluid complex coacervate containing a contrast agent such as titanium particles will be more viscous at low shear rates than the same fluid complex coacervate that does not include the titanium particles (see for example FIG. 9). Furthermore, the viscosity of the fluid complex coacervate can recover at low shear rates. Reversible shear thinning allows the viscous fluid complex coacervates described herein to be injected through a long narrow catheter with low force, and as the shear rate decreases to zero at the catheter exit, the viscosity of the complex coacervate increases to prevent it from flowing away from the application site. This allows precise control while injecting the composition.

In one aspect, the in situ solidifying complex coacervates and adhesive solids and gels produced therefrom can be used to reinforce the inner wall of a blood vessel in the subject. The in situ solidifying complex coacervate can be introduced into the vessel at a sufficient amount to coat the inner lining of the vessel so that the vessel is not blocked. For example, the in situ solidifying complex coacervate can be injected into a vessel where there is an aneurysm. Here, the in situ solidifying complex coacervate reduce or prevents the rupture of an aneurysm. In one aspect, the fluid complex coacervate can include a contrast agent. The contrast agents and methods for visualizing discussed above can be used in this embodiment.

In one aspect, the in situ solidifying complex coacervates and adhesive solids and gels produced therefrom can be used to close or seal a puncture in a blood vessel in the subject. In one aspect, the in situ solidifying complex coacervate can be injected into a vessel at a sufficient amount to close or seal the puncture from within the vessel so that the vessel is not blocked. In another embodiment, the in situ solidifying complex coacervate can be applied to puncture on the exterior surface of the vessel to seal the puncture. In one aspect, the fluid complex coacervate can include a contrast agent. The contrast agents and methods for visualizing discussed above can be used in this embodiment.

In one aspect, the in situ solidifying complex coacervates and adhesive solids and gels produced therefrom can be used to repair a number of different bone fractures and breaks. The adhesive solids and gels upon formation adhere to bone (and other minerals) through several mechanisms. The surface of the bone's hydroxyapatite mineral phase ($Ca_5(PO_4)_3(OH)$) is an array of both positive and negative charges. The negative groups present on the polyanion (e.g., phosphate groups) can interact directly with the positive surface charges or it can be bridged to the negative surface charges through the cationic groups on the polycation and/or multivalent cations. Likewise, direct interaction of the polycation with the negative surface charges would contribute to adhesion. Alternatively, oxidized crosslinkers can couple to nucleophilic sidechains of bone matrix proteins.

Examples of such breaks include a complete fracture, an incomplete fracture, a linear fracture, a transverse fracture, an oblique fracture, a compression fracture, a spiral fracture, a comminuted fracture, a compacted fracture, or an open fracture. In one aspect, the fracture is an intra-articular fracture or a craniofacial bone fracture. Fractures such as intra-articular fractures are bony injuries that extend into and fragment the cartilage surface. The adhesive solids and gels produced from the in situ solidifying complex coacervates may aid in the maintenance of the reduction of such fractures, allow less invasive surgery, reduce operating room time, reduce costs, and provide a better outcome by reducing the risk of post-traumatic arthritis.

In other aspects, the in situ solidifying complex coacervates and adhesive solids and gels produced therefrom can be used to join small fragments of highly comminuted fractures. In this aspect, small pieces of fractured bone can be adhered to an existing bone. It is especially challenging to maintain reduction of the small fragments by drilling them with mechanical fixators. The smaller and greater the number of fragments the greater the problem. In one aspect, the in situ solidifying complex coacervates may be injected in small volumes to create spot welds as described above in order to fix the fracture rather than filling the entire crack. The small biocompatible spot welds would minimize interference with healing of the surrounding tissue and would not necessarily have to be biodegradable. In this respect it would be similar to permanently implanted hardware.

The in situ solidifying complex coacervates and adhesive solids and gels produced therefrom have numerous dental applications. For example, the in situ solidifying complex coacervates and adhesive solids and gels produced therefrom can be used to seal breaks or cracks in teeth, for securing crowns, or allografts, or seating implants and dentures. The in situ solidifying complex coacervate can be applied to a specific points in the mouth (e.g., jaw, sections of a tooth) followed by attaching the implant to the substrate and subsequent curing.

In other aspects, the in situ solidifying complex coacervates and adhesive solids and gels produced therefrom can adhere a substrate to bone other tissues such as, for example, cartilage, ligaments, tendons, soft tissues, organs, and synthetic derivatives of these materials. For example, implants made from titanium oxide, stainless steel, or other metals are commonly used to repair fractured bones. The in situ solidifying complex coacervate can be applied to the metal substrate, the bone, or both prior to adhering the substrate to the bone. In other aspects, the substrate can be a fabric (e.g., an internal bandage), a tissue graft, a patch, or a wound healing material. Thus, in addition to bonding bone fragments, the in situ solidifying complex coacervates and adhesive solids and gels produced therefrom can facilitate the bonding of substrates to bone, which can facilitate bone repair and recovery. Using the fluid coacervate complexes and spot welding techniques described herein, the in situ solidifying complex coacervates and adhesive solids and gels produced therefrom can be used to position biological scaffolds in a subject. Small adhesive tacks composed of the adhesive complex coacervates described herein would not interfere with migration of cells or transport of small molecules into or out of the scaffold. In certain aspects, the scaffold can contain one or more drugs that facilitate growth or repair of the bone and tissue. In other aspects, the scaffold can include drugs that prevent infection such as, for example, antibiotics. For example, the scaffold can be coated with the drug or, in the alternative, the drug can be incorporated within the scaffold so that the drug elutes from the scaffold over time.

It is also contemplated that the adhesive gels and solids produced from the in situ solidifying complex coacervates described herein can encapsulate, scaffold, seal, or hold one or more bioactive agents. The bioactive agents can be any drug including, but not limited to, antibiotics, pain relievers, immune modulators, growth factors, enzyme inhibitors, hormones, mediators, messenger molecules, cell signaling molecules, receptor agonists, oncolytics, chemotherapy agents, or receptor antagonists. The agent may also be autologous or homologous (allogeneic) cells, platelet rich plasma (PRP), or other like tissue.

In another aspect, the bioactive agent can be a nucleic acid. The nucleic acid can be an oligonucleotide, deoxyribonucleic acid (DNA), ribonucleic acid (RNA), or peptide nucleic acid (PNA). The nucleic acid of interest can be nucleic acid from any source, such as a nucleic acid obtained from cells in which it occurs in nature, recombinantly produced nucleic acid, or chemically synthesized nucleic acid. For example, the nucleic acid can be cDNA or genomic DNA or DNA synthesized to have the nucleotide sequence corresponding to that of naturally-occurring DNA. The nucleic acid can also be a mutated or altered form of nucleic acid (e.g., DNA that differs from a naturally occurring DNA by an alteration, deletion, substitution or addition of at least one nucleic acid residue) or nucleic acid that does not occur in nature.

In other aspects, the bioactive agent is used in bone treatment applications. For example, the bioactive agent can be bone morphogenetic proteins (BMPs) and prostaglandins. When the bioactive agent is used to treat osteoporosis, bioactive agents known in the art such as, for example, bisphonates, can be delivered locally to the subject by the in situ solidifying complex coacervates and adhesive solids and gels produced therefrom.

In certain aspects, the filler used to produce the in situ solidifying complex coacervate can also possess bioactive properties. For example, when the filler is a silver particle, the particle can also behave as an anti-microbial agent. The rate of release can be controlled by the selection of the materials used to prepare the complex, as well as the charge of the bioactive agent if the agent has ionizable groups. Thus, in this aspect, the adhesive solid or gel produced from the in situ solidifying complex coacervate can perform as a localized controlled drug release depot. It may be possible to simultaneously fix tissue and bones as well as deliver bioactive agents to provide greater patient comfort, accelerate bone healing, and/or prevent infections.

The adhesive complex coacervates and adhesives produced therefrom can be used in a variety of other surgical procedures. For example, the in situ solidifying complex coacervates can be applied as a covering to a wound created by the surgical procedure to promote wound healing and prevent infection. In one aspect, the in situ solidifying complex coacervates and adhesive solids and gels produced therefrom can be used to treat ocular wounds caused by trauma or by the surgical procedures. In one aspect, the in situ solidifying complex coacervates and adhesives produced therefrom can be used to repair a corneal or schleral laceration in a subject. In other aspects, the in situ solidifying complex coacervates can be used to facilitate healing of ocular tissue damaged from a surgical procedure (e.g., glaucoma surgery or a corneal transplant). The methods disclosed in U.S. Published Application No. 2007/0196454, which are incorporated by reference, can be used to apply the coacervates described herein to different regions of the eye.

The in situ solidifying complex coacervates and adhesive solids and gels produced therefrom can be used to seal the junction between skin and an inserted medical device such as catheters, electrode leads, needles, cannulae, osseo-integrated prosthetics, and the like. Here, upon insertion and/or removal of the medical device the fluid complex coacervate is applied to the junction between the skin of the subject and the inserted medical device in order to seal the junction. Thus, the fluid complex coacervate prevent infection at the entry site when the device is inserted in the subject and subsequently forms a solid or gel. In other aspects, the in situ solidifying complex coacervates can be applied to the entry site of the skin after the device has been removed in order to expedite wound healing and prevent further infection.

In another aspect, the in situ solidifying complex coacervates and adhesive solids and gels produced therefrom can be used to prevent or reduce the proliferation of tumor cells during tumor biopsy. The method involves back-filling the track produced by the biopsy needle with the in situ solidifying complex coacervates upon removal of the biopsy needle. In one aspect, the in situ solidifying complex coacervates includes an anti-proliferative agent that will prevent or reduce the potential proliferation of malignant tumor cells to other parts of the subject during the biopsy.

In another aspect, the in situ solidifying complex coacervates and adhesive solids and gels produced therefrom can be used to close or seal a puncture in an internal tissue or membrane. In certain medical applications, internal tissues or membranes are punctured, which subsequently have to be sealed in order to avoid additional complications. Alternatively, the in situ solidifying complex coacervates and adhesive solids and gels produced therefrom can be used to adhere a scaffold or patch to the tissue or membrane in order to seal the tissue, prevent further damage and facilitate wound healing.

In another aspect, the in situ solidifying complex coacervates and adhesive solids and gels produced therefrom can be used to seal a fistula in a subject. A fistula is an abnormal connection between an organ, vessel, or intestine and another structure such as, for example, skin. Fistulas are usually caused by injury or surgery, but they can also result from an infection or inflammation. Fistulas are generally a disease condition, but they may be surgically created for therapeutic reasons. In other aspects, the in situ solidifying complex coacervates and adhesive solids and gels produced therefrom can prevent or reduce undesirable adhesion between two tissues in a subject, where the method involves contacting at least one surface of the tissue with the in situ solidifying complex coacervate. In one aspect, the fistula is an enterocutaneous fistula (ECF). ECF is an abnormal connection that develops between the intestinal tract or stomach and the skin. As a result, contents of the stomach or intestines leak through to the skin. Most ECFs occur after bowel surgery.

In certain aspects, after the adhesive solid or gel has been produced from the in situ solidifying complex coacervates, the adhesive solid or gel can be subsequently cured by covalently crosslinking the polycation and/or polyanion having crosslinkable groups in the solid or gel. Depending upon the selection of starting materials, varying degrees of crosslinking can occur throughout the coacervate during curing. The adhesive gel can be exposed to heat or light in order to facilitate crosslinking. Any of the initiators described herein can be included in the in situ solidifying complex coacervates to facilitate covalent crosslinking.

In addition to medical biological application, the in situ complex coacervates can be incorporated in a number of other articles and compositions that contain water or that will be exposed to an aqueous environment. For example, the in situ solidifying complex coacervates can be used as underwater coating or paint. In one aspect, the in situ solidifying complex coacervate can be applied to a submerged surface in a freshwater or marine environment and would rapidly solidify to form a protective coating on the surface. For example, the in situ solidifying complex coacervates can be used in marine applications, where the monovalent salt concentration can be very high. Here, the monovalent salt concentration in the in situ solidifying complex coacervate can be adjusted so that the in situ solidifying complex coacervate will form an insoluble gel or solid when it comes into contact with seawater. In one aspect, the adhesive gel or solid can be covalently crosslinked by natural ambient light or by applying a light source. Crosslinking groups on the polycation and/or polyanion would allow the coating to be covalently crosslinked after application and gelation to increase hardness and improve strength and stability.

In other aspect, the other articles can include a cured adhesive complex coacervate described herein. For example, the in situ solidifying complex coacervate can be applied to a film substrate to create an adhesive tape. In this aspect, the application of the complex coacervate and ultimately the adhesive solid or gel is performed in an aqueous environment and does not require the removal of organic solvents typically used to prepare adhesive backings.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Protamine Methacrylation

Protamine sulfate from salmon sperm (MP Biomedical, cat #0210275280) was dissolved in 150 mM NaCl solution at 50 mg/ml. The pH was adjusted to 6.5 with NaOH. A ten-fold molar excess of glycidyl methacrylate was added dropwise while stirring at 20° C. The pH was adjusted to 6.5 every 12 hrs. After 48 hrs the salmine was precipitated with 10-fold excess volume of acetone. The precipitate was rinsed with acetone, dried, and re-dissolved in water. After dialysis for 48 hr the pH was adjusted to 7 and the solution was lyophilized. Methacrylation on the C-terminal carboxylate was verified by NMR spectroscopy.

Protamine Analogs: Synthetic Guanidinyl Polymers

Analogs of arginine-rich protamines were synthesized by free radical copolymerization of N-(3-methacrylamidopropyl) guanidinium chloride with acrylamide. The major advantages of synthetic polyguanidinium over natural protamines are (1) the guanidinyl sidechain density, and thereby the polymer charge density, can be varied over a wide range to adjust gelation conditions, (2) the MW can be controlled and varied, (3) the guanidinyl monomer can be copolymerized with other monomers with sidechains that add additional functionality to the polymers, such as crosslinking groups or fluorescent labels, and (4) synthetic acrylate protamine analogs are non-degradable or slowly degradable for applications in which biodegradability is not desirable.

Figure 5:
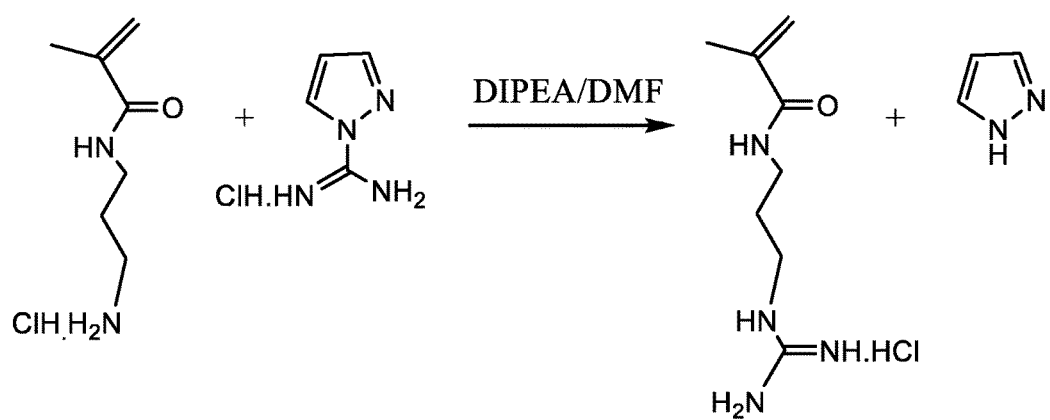
FIG. 5 shows the synthesis of N-(3-methacrylamidopropyl) guanidinium chloride.

FIG. 5 shows the reaction scheme for preparing an exemplary synthetic guanidinyl monomer. N-(3-methacrylamidopropyl)guanidinium chloride was synthesized following published procedures. 1H-pyrazole-1-carboxamidine monohydrochloride (12.3 g, 84 mmol) was added under Ar to a stirred solution of N-(3-aminopropyl)methacrylamide hydrochloride (15 g, 84 mmol), 4-methoxyphenol (150 mg) and N,N-diisopropylethylamine (38 mL, 209 mmol) in DMF (85 mL, keeping the final concentration of the reactants 2M). The mixture was stirred at room temperature for 24 h under Ar, then poured into diethylether (1200 mL). The resulting oil phase was separated from the supernatant and washed twice with a solution of acetonitrile (200 mL) and triethylamine (10 mL). The resulting solid was washed with dichloromethane (300 mL) and dried under vacuum to yield 13.3 g (72%) of the product. $^1$H NMR (400 MHz, DMSO-$d_6$) δ ppm 8.09 (s, 1H), 7.91 (s, 1H), 7.70-6.90 (br, 4H), 5.70 (s, 1H), 5.33 (s, 1H), 3.16 (m, 4H), 1.87 (s, 3H), 1.65 (quin, 3H).

Polyguanidine (FIG. 6A) was synthesized by dissolving N-(3-methacrylamidopropyl)guanidinium chloride, acrylamide, fluorescein O-methacrylate and 4-cyano-4-(thiobenzoylthio)pentanoic acid in DMSO. After degassing for 30 min, the initiator azobisisobutyronitrile was added and the solution heated to 70° C. under Ar. After 40 h, the solution was cooled, precipitated with acetone, and dissolved in water. Degassed for 30 min, added 2,2'-Azobis[2-(2-imidazolin-2-yl)propane]dihydrochloride, and heated at 70° C. overnight to remove the 4-cyano-4-(thiobenzoylthio)pentanoic acid RAFT agent. The polymer solution was purified by dialysis (MWCO-14,000) against dI water for 3 days, then lyophilized.

Methacrylamide sidechains were grafted onto polyguanidine (FIG. 6B) to facilitate crosslinking of the polymers. Polyguanidium was dissolved in methanol. Triethylamine and the inhibitor phenothiazine were added. The solution was cooled to 0° C. before addition of methacryloyl chloride. The reaction was removed from the ice bath and stirred at room temperature overnight. The polymer was precipitated with acetone, filtered, and dried.

Polyphosphates

In one embodiment, polyphosphates were used to form complex coacervates with protamine or polyguanidine. Negatively charged phosphate and phosphonate groups form strong electrostatic bonds with guanidium groups. Several polyphosphates are commercially available and are used as additives to food and consumer health care products. Sodium hexametaphosphate (CAS #68915-31-1) was used to form the salmine complex coacervates. Other suitable polyphosphates include sodium triphosphate (CAS #7758-29-4) and sodium inositol hexaphosphate (CAS #14306-25-3), which is also known as phytic acid. These polyphosphates are biodegradable and non-toxic. Inositol hexaphosphate occurs naturally in plants and is sold and consumed as a neutriceutical.

Preparation of Coacervates

The sodium salt of poly(acrylamide-co-acrylamidohexanoic acid), comprising 45.8 mol % acrylamidohexanoic acid sidechains, was dissolved at 50 mg/ml in separate solutions of 150, 300, 500, 750, and 1000 mM NaCl. Salmine sulfate (MP Biomedicals) was dissolved at 50 mg/ml in separate solutions of 150, 300, 500, 750, and 1000 mM NaCl. Complex coacervates were formed by adding an appropriate volume of the salmine solution at a given NaCl concentration drop wise to an appropriate volume of the poly(acrylamide-co-acrylamidohexanoic acid) such that the final charge ratio was 1:1 carboxylate to arginine. The mixed solution turned immediately cloudy and within a few minutes the complex coacervate began to settle out on the bottom of the tube. The complex coacervate phase was allowed to equilibrate for 24 hr, after which the polymer-depleted upper aqueous phase is removed. The dense lower phase is used as the in situ solidifying complex coacervate. 150 micro liters of the dense complex coacervate phase was pipetted onto the deck of the rheometer with a positive displacement pipette.

Figure 2:
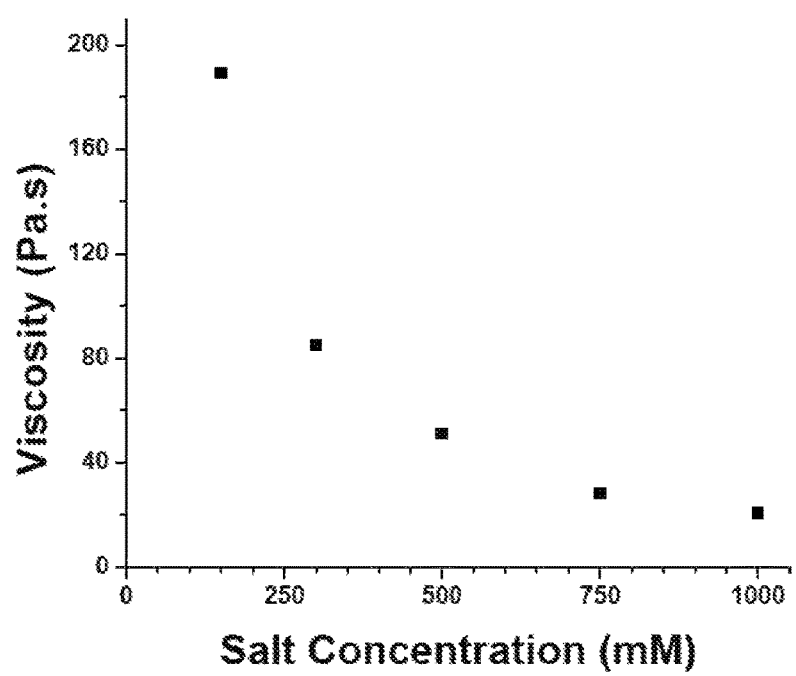
FIG. 2 shows viscosity versus ionic strength of a synthetic polyphosphate and protamine mixed at a 1:1 macroion charge ratio.

The effect of ionic strength on the material properties of the associated PEs is further illustrated in FIG. 2. The viscosity of the materials changed by an order of magnitude in going from the in situ solidifying complex coacervate at high ionic strength to a solid gel near physiological ionic strength.

Example 2

Using the procedure of Example 1, aqueous solutions of salmine and hexametaphosphate were mixed in various concentrations of NaCl at room temperature, 22° C. Between 1100 and 1200 mM NaCl a critical ionic strength (I) exists at which the complex coacervate becomes a solid non-flowing gel. The viscosity of the coacervate decreases with increasing I above $I_{crit}$. The stiffness of the gels increases below $I_{crit}$. The forms are interconvertible by changing the ionic strength. The results are depicted in FIG. 1.

Evaluation of In Situ Solidifying Complex Coacervates as Embolic Agents

Figure 3:
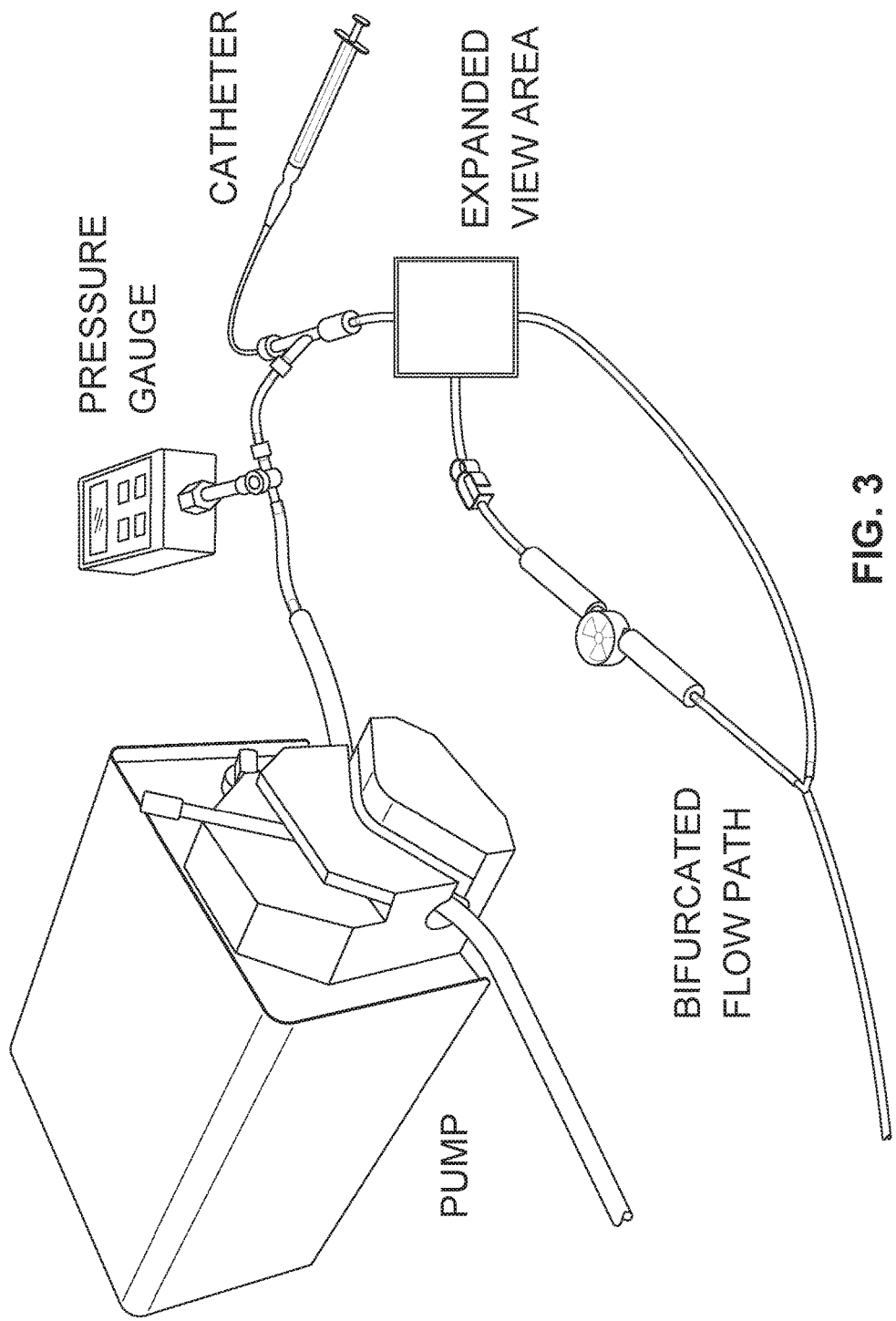
FIG. 3 shows an in vitro vascular model with a bifurcated flow path. A narrow catheter was inserted into one side of the flow path for in flow injection of an adhesive complex coacervate. By closing the opposite side, the pressure maintained by the embolism can be determined.
Figure 4A:
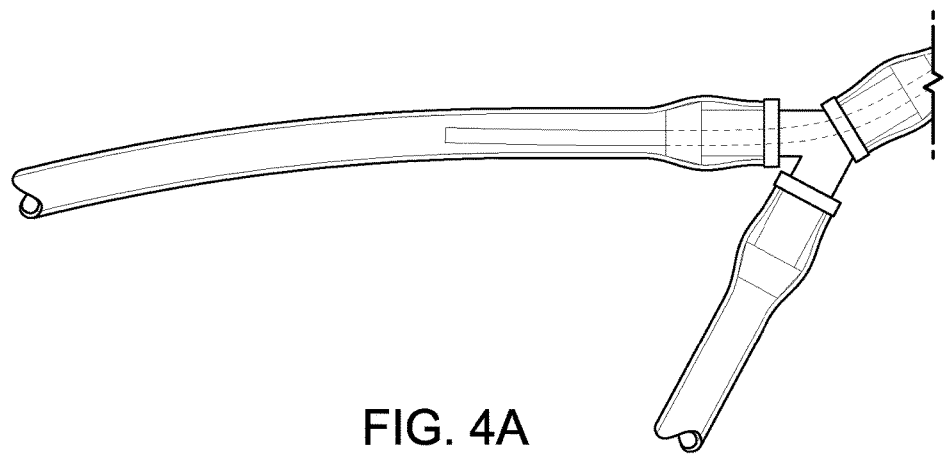
FIGS. 4A-4C show the use of an in situ solidifying complex coacervate as embolic agent in an in vitro model composed a bifurcated vascular system created with silicone tubing and a peristaltic pump.
Figure 4B:
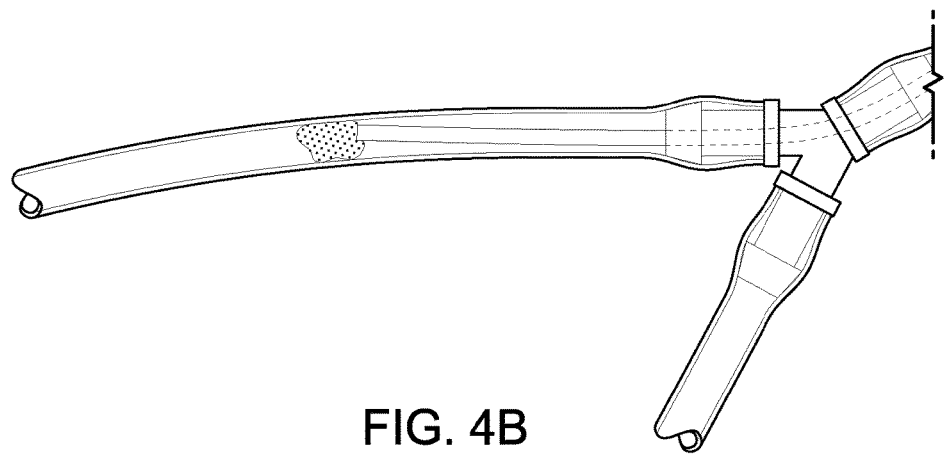
Figure 4C:
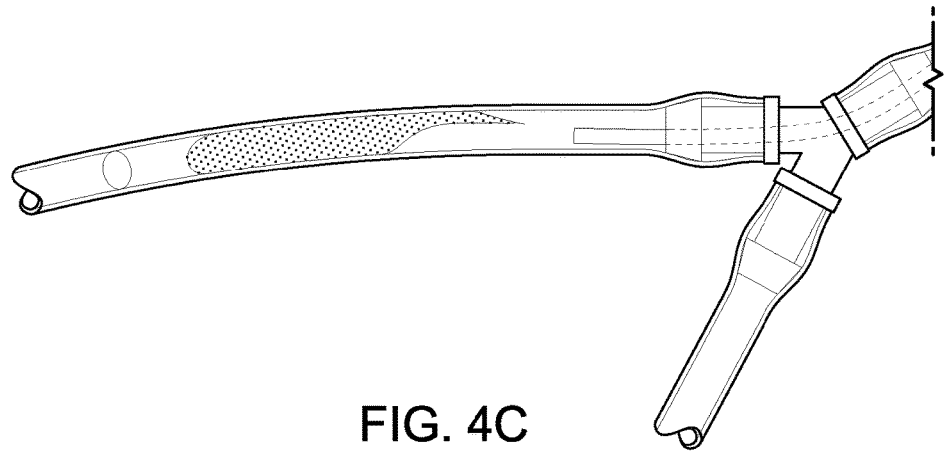

The use of the in situ solidifying complex coacervates (salmine and hexametaphosphate) as embolic agent in an in vitro model is demonstrated in FIGS. 3 and 4. A model of a bifurcated vascular system was created with silicone tubing and a peristaltic pump. The system includes a pressure gauge, valves for flow control, and an inlet for small diameter catheters (FIG. 3). While circulating physiological saline, a narrow gauge catheter (blue) was inserted into one side of the bifurcated channel (FIG. 4A). A fluid high ionic strength (1,200 mM NaCl) in situ solidifying complex coacervate injected into the physiological saline flow immediately solidified (FIG. 4B). Flow through the channel was diverted to the other channel, which is evident from the stationary bubble below the gelled plug (FIG. 4C, white arrow). To determine the pressure the embolic plug could withstand, the open channel was clamped to build pressure. The plug withstood a closed system pressure of 110 mm of Hg before failing in the example shown. This is within normal physiological blood pressure for a healthy human.

Example 3. In Vivo Evaluation of In Situ Setting Adhesive Coacervates: Rabbit Kidney Embolization A New Zealand white female rabbit weighing 4.5 kg was kept in an environmentally controlled animal research facility. Food was offered once a day and water was provided ad libitum. This investigation was carried out under an IACUC approved protocol and following the University of Utah animal research guidelines.

All surgical procedures were performed under sterile conditions. The rabbit was first anesthetized with Isoflurane in an induction chamber, then intubated with an endotracheal tube (3.5 mm, Hudson/Sheridan). Once intubated, the rabbit was connected to an anesthetic machine (Drager Narkomed 2B) equipped for non-invasive monitoring, including an anesthetic gas analyzer, respiratory monitor (Ohmeda 5250 RGM), oximeter, thermometer, and Isoflurane vaporizer. An intravenous infusion of 0.9% saline solution (Baxter) was administered during the procedure.

Preparation of In Situ Solidifying Coacervate

Complex coacervates were prepared using protamine sulfate (MP Biomedicals, Inc.) and sodium phytate (Sigma-Aldrich, Inc.). Protamine sulfate (PRT) and sodium phytate (IP6) were dissolved in 1200 mM NaCl at 62.5 mg/mL and 115.1 mg/mL, respectively, and adjusted to pH 7.2. The solutions were filter sterilized into sterile 50 mL conical tubes through a 0.22 μm syringe filter (Millex-GS, Millipore). The solutions, 8 mL of IP6 and 32 mL PRT, were mixed at a 1:1 positive to negative charge ratio at 60° C., above the coacervation phase separation temperature. Tantalum metal powder (1,114.3 mg, 1-5 micron particle size, Atlantic Equipment Engineers) was also added so that the condensed coacervate phase was 30 wt % tantalum. The solution was mixed continuously as it cooled to room temperature. The dense coacervated settled to the bottom on the tube. After 24 hr, the supernatant and removed and the dense coacervate phase was aseptically loaded into 1 mL syringes.

Catheterization Procedure

The right femoral artery was chosen as the site of arterial catheterization. The inner side of the leg was shaved, and the incision site and surrounding skin was cleaned with 70% isopropyl alcohol. The disinfected area was covered with sterile drapes, exposing only the area overlying the right femoral artery. The artery was exposed with a 3-5 cm longitudinal incision. The location of the incision was determined by palpating the artery. The artery was isolated from the femoral nerve and vein by blunt dissection. Two 4.0 silk sutures were positioned under the artery and used to gently elevate the artery for access. Topical Lidocain (2%, Hospira) was administered to decrease the vasospasm of the femoral artery during handling.

The femoral artery was accessed using a 4F access kit (Access Point Technology, Inc). The micro-catheter (2.8 F, 135 cm/Biomerics) was maneuvered from the femoral artery into the renal artery under fluoroscopy (C-arm 9800 series OEC MEdical/GE medical). Omnipaque (Iohexol 240 mg/ml) was used as the X-ray contrast agent to visualize organs and blood vessels. Once the microcatether was positioned in the renal artery, Omnipaque diluted 1:1 with normal saline was injected to visualize the blood vessels. The catheter was flushed with saline, then 0.2 mL of hypersaline (1.2M) was injected into the catether.

Figures 7A, 7B, 7C, 7D:
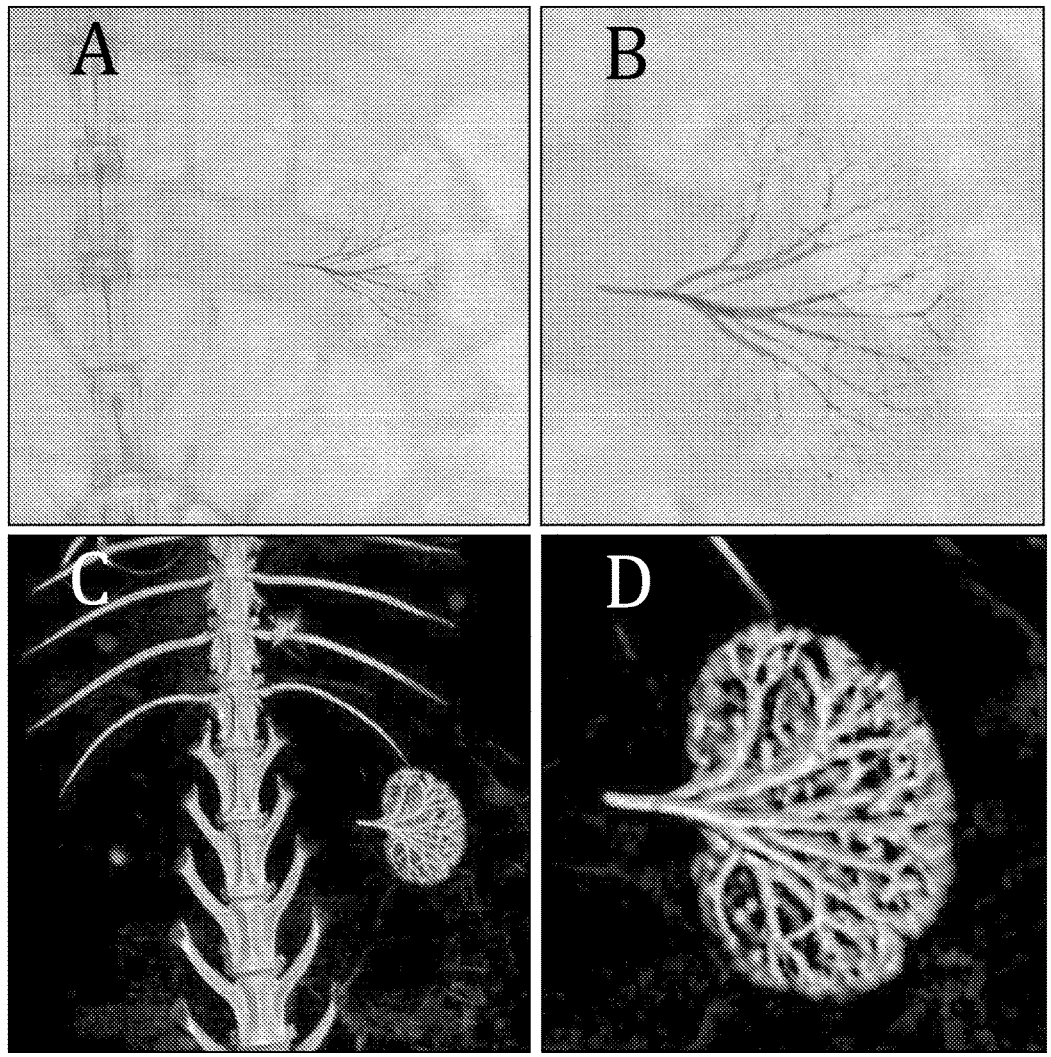
FIGS. 7A and 7B show fluoroscopic images of embolized kidney.
FIGS. 7C and 7D show the three dimensional CT images of embolized kidney post mortem.
Figures 8A, 8B, 8C, 8D:
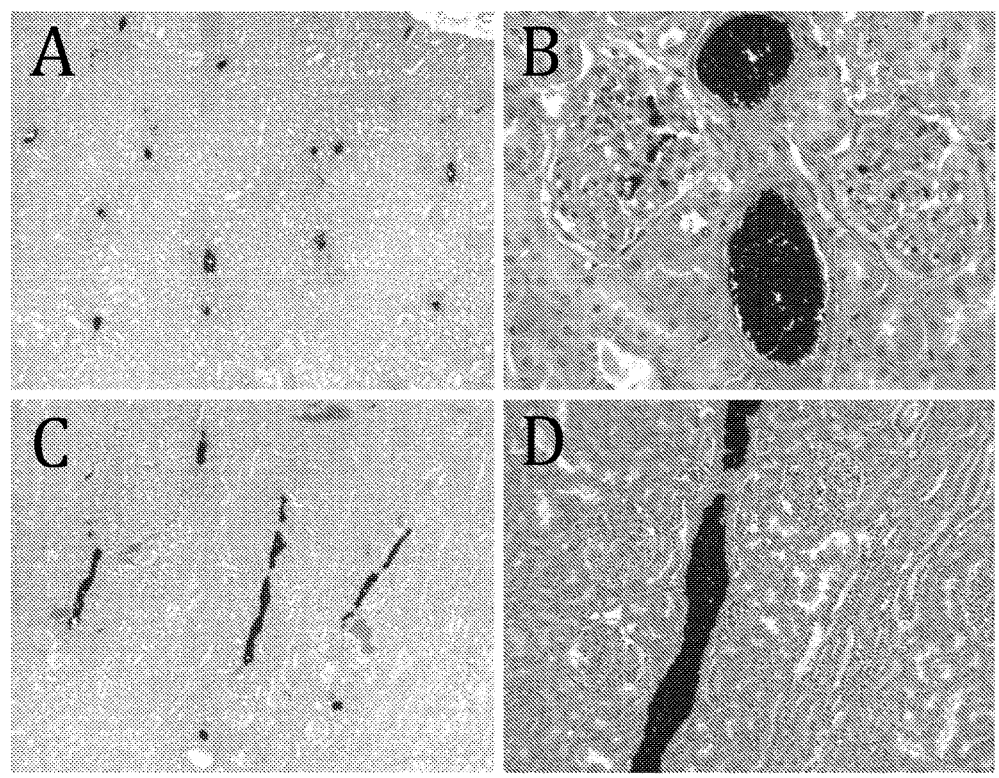
FIG. 8A shows low magnification of cross-sectioned occluded arterioles in the cortex of an embolized kidney.
FIG. 8B shows higher magnification of glomerulus with occluded arterioles and capillaries of an embolized kidney.
FIG. 8C shows low magnification of longitudinal-sectioned occluded arterioles in the cortex of an embolized kidney.
FIG. 8D shows higher magnification of occluded arteries of an embolized kidney.

The in situ solidifying adhesive coacervate was loaded into a 1 mL syringe (Medallion, Merit Medical). The coacervate contained 30 wt % tantalum metal (1-5 micron particle size) as a contrast agent. The syringe was attached to the catheter and the sample was injected into the renal artery. No changes in breathing or heart rate occurred during or after the embolization. Injection of the adhesive was visualized using a C-arm 9800 series fluoroscope (OEC Medical/GE Medical Inc.). Complete occlusion of the left kidney was observed as a result of injecting the adhesive (FIGS. 7A and 7B). It was apparent the coacervate evenly penetrated into the fine branching blood vessels of the entire kidney cortex.

The animal was euthanized 90 min after embolization with Euthanasia solution (Vet One). No changes were observed by fluoroscopy in the position or opaqueness of the in situ solidifying coacervate during the 90 minutes post injection. Post mortem, the animal was scanned on an Axiom Artist dBA biplane angiography system (Siemens Inc.) to obtain a 3D image of the embolized kidney (FIGS. 7C and 7D). Complete and uniform embolization was apparent in the 3D images.

Histology

During necropsy, the embolized kidney was isolated and fixed in 10% buffered formalin. After 2 days, the renal capsule was removed and the tissue was fixed for another 4 days. The tissue was embedded in paraffin, sectioned and stained with Hematoxylin & Eosin (FIGS. 8A-8D). From histology, it was observed that arteries and small arteries were fully occluded. Occlusion occurred uniformly throughout the kidney, penetrating into the capillaries of glomeruli. Importantly, no embolic agent was visible in veins or venules. The adhesive coacervate appeared to adhere to the wall of the blood vessels. The adhesive coacervate did not mix with blood, and there was no evidence of lysis of red blood cells in direct contact with the adhesive. There was no visible effect on cells or tissues immediate adjacent to the emboli.

Example 4. Flow Behavior Studies

Sample Preparation

Complex coacervates were prepared using protamine sulfate (MP Biomedicals, Inc.) and sodium phytate (Sigma-Aldrich, Inc.). Protamine sulfate (PRT) and sodium phytate (IP6) were dissolved in 1,200 mM NaCl at concentrations of 62.5 mg/mL and 115.1 mg/mL, respectively, and adjusted to pH 7.2. The solutions were mixed at a ratio of 1 part IP6 to 4 parts PRT to give a 1:1 positive to negative charge ratio. The solutions were mixed at 60° C., above the coacervation phase separation temperature. An amount of tantalum metal powder (1-5 micron particle size, Atlantic Equipment Engineers) was added so that the condensed coacervate phase contained 30 wt % tantalum. The solution was mixed continuously as it cooled to room temperature. The dense coacervate phase settled to the bottom on the tube. After 24 hr, the supernatant phase was removed from the coacervate phase.

Oscillatory Rheology

Figure 9:
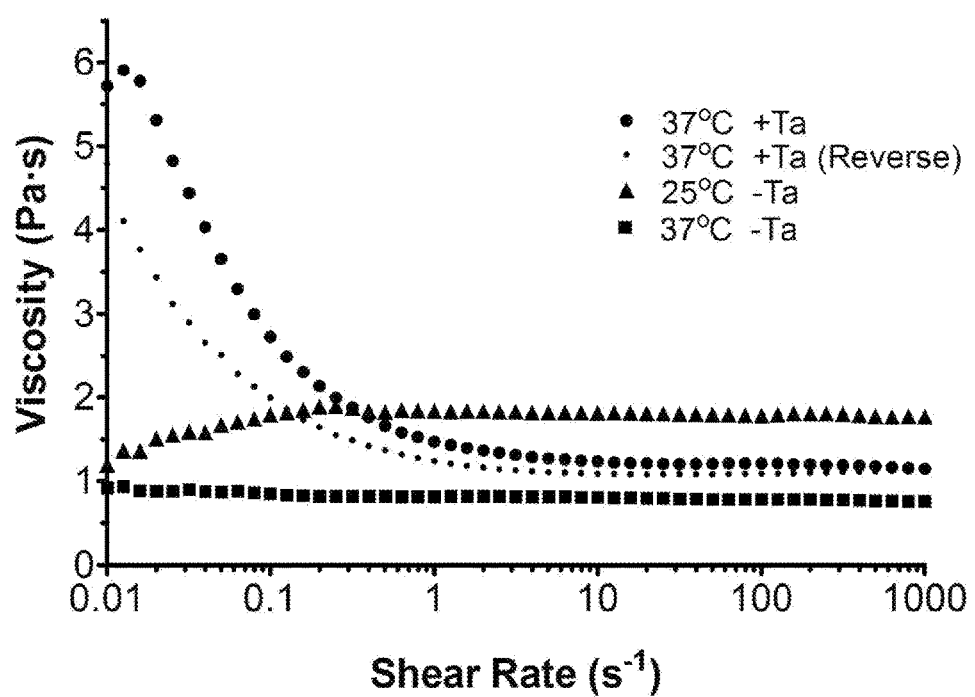
FIG. 9 shows the flow behavior of PRT/IP6 complex coacervates with and without 30 wt % tantalum contrast agent.

The flow behavior of PRT/IP6 coacervates was characterized on a temperature controlled rheometer (AR 2000ex Rheometer, TA Instruments). Viscosity was measured as a function of applied shear rate using a 20 mm, 4° cone geometry. A solvent trap was used to prevent the sample from drying out during the experiment. Shear rate was stepped from $0.01$ $s^{-1}$ to $1000$ $s^{-1}$ at 10 points per decade. The tantalum containing coacervates were 5-6 times more viscous at low shear rates than the non-tantalum containing coacervates. The tantalum coacervate shear-thinned to ~1.2 Pa·s as the shear rate increased, approaching the viscosity of the non-tantalum coacervates at high shear rates (FIG. 9). At the end of the forward sweep, the shear rate was stepped back down from $1000$ $s^{-1}$ to $0.01$ $s^{-1}$. The viscosity of the tantalum coacervate recovered at low shear rates. Reversible shear thinning is a critical feature of the contrast containing coacervates; it allows the viscous composition to be injected through a long narrow catheter with low force, and as the shear rate decreases to zero at the catheter exit, the viscosity of the composition increases to prevent it from flowing away from the application site. This allows precise control while injecting the composition.

Example 5. In Situ Solidifying Adhesive Phase Diagram

Aqueous mixtures of oppositely charged polyelectrolytes (PEs) can exist in several material states, or forms. The form depends on solution conditions like pH, ionic strength, and temperature. A phase diagram of mixtures of protamine sulfate (PRT) and sodium phytate (IP6) with positive to negative charge ratios ranging from 6:1 to 1:6, and solution ionic strengths ranging from 0.15 to 1.5 M NaCl, was created at 21° C. and 37° C. (FIG. 10). Solutions (1 ml) were made in 1.5 mL Eppendorf tubes at 60° C. by combining appropriate volumes of 100 mg/mL stock solutions of PRT and IP6 at pH 7.2, 5 M NaCl, $H_2O$. PRT was added dropwise to the other components while vortexing. The solutions were incubated at 37° C. As the solutions cooled to 37° C. the PEs condensed and separated into dense fluid (coacervate) or solid (gel) phases. After equilibrating at 37° C. for 24 hr, the form of the condensed PE phase were visibly scored as coacervate or gel by whether it flowed when tilted (coacervate) or not (gel). The solutions were then cooled to 21° C. and scored again after 24 hr.

The form of the electrostatically associated oppositely charged PEs is dependent on the NaCl concentration. Higher salt concentrations shield electrostatic interactions and decrease the strength of the PE association, resulting in a fluid coacervate form. At low salt, the interactions are stronger, resulting in strongly associated solid gel forms. At very high salt concentrations the PE charges are fully shielded and the PEs do not associate. In this case the PEs are fully solvated and suspended in the aqueous solution; no phase separation occurs. Temperature also affects the strength of the PE association. At higher temperatures the electrostatic interactions are weaker and hence the PEs condense into a liquid coacervate form at lower NaCl concentrations. The strength of the association between PEs is highest when the maximum number of charge interactions occurs, which is when the charge ratio is 1:1.

The phase diagrams illustrate the principle of the invention. By mixing PEs in a region of the phase diagram in which fluid complex coacervates condense, the adhesive can be prepared in an injectable fluid form. If the fluid form is injected into an environment corresponding to a gel region of the phase diagram, the fluid form will harden into a solid gel as the adhesive equilibrates to the new solution conditions. From the phase diagrams in FIG. 10, it can be observed that a fluid coacervate form of the adhesive can be prepared at NaCl concentrations ranging from 600 mM to 1,500 mM. When the fluid coacervate is injected into an environment with less than 300 mM NaCl at 37° C., i.e., human physiological conditions, the fluid form will spontaneously transition to a solid gel form in situ.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. An adhesive fluid complex coacervate comprising water, at least one polycation, at least one polyanion, and a salt that produces monovalent ions in water, wherein the salt is sodium chloride, and wherein the concentration of the monovalent ions in the adhesive fluid complex coacervate is greater than the concentration of the monovalent ions present at an application site, and wherein the polycation is synthetic polyguanidinyl polymer comprising an acrylate, methacrylate, acrylamide, or methacrylamide backbone and two or more guanidinyl groups pendant to the backbone.

2. The adhesive fluid complex coacervate of claim 1, wherein the concentration of the monovalent ions in the complex coacervate is 1.5 to 10 times greater than the concentration of the monovalent ions at the application site.

3. The adhesive fluid complex coacervate of claim 1, wherein the total positive/negative charge ratio of the polycation to the polyanion is from 4 to 0.25 and the concentration of the monovalent ions in the complex coacervate is from 0.5 M to 2.0 M.

4. The adhesive fluid complex coacervate of claim 1, wherein the adhesive fluid complex coacervate has a pH of 6 to 9.

5. The adhesive fluid complex coacervate of claim 1, wherein the polycation is a synthetic polyguanidinyl polymer comprising a copolymer of a monomer selected from the group consisting of an acrylate, a methacrylate, an acrylamide, a methacrylamide, or any combination thereof and a compound of formula I

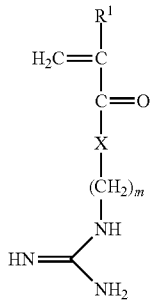

wherein $R^1$ is hydrogen or an alkyl group, X is oxygen or $NR^5$, where $R^5$ is hydrogen or an alkyl group, and m is from 1 to 10, or the pharmaceutically-acceptable salt thereof.

6. The adhesive fluid complex coacervate of claim 5, wherein the polycation comprises polymerization product between the compound of formula I and methacrylamide.

7. The adhesive fluid complex coacervate of claim 5, wherein $R^1$ is methyl, X is NH, m is 3.

8. The adhesive fluid complex coacervate of claim 1, wherein the polyanion comprises a polyphosphate.

9. The adhesive fluid complex coacervate of claim 1, wherein the polyanion is an inorganic polyphosphate or a phosphorylated sugar.

10. The adhesive fluid complex coacervate of claim 1, wherein the polyanion comprises a hexametaphosphate salt.

11. The adhesive fluid complex coacervate of claim 1, wherein the polyanion is inositol hexaphosphate.

12. The adhesive fluid complex coacervate of claim 1, wherein the polyanion comprises phosphate groups and/or phosphonate groups.

13. The adhesive fluid complex coacervate of claim 1, wherein the polyanion comprises a polyacrylate comprising two or more pendant phosphate or phosphonate groups.

14. The adhesive fluid complex coacervate of claim 1, wherein the polyanion is the copolymerization product between a phosphate or phosphonate acrylate and/or phosphate or phosphonate methacrylate with one or more additional polymerizable monomers.

15. The adhesive fluid complex coacervate of claim 1, wherein the adhesive fluid complex coacervate further comprises a contrast agent or a visualization agent.

16. The adhesive fluid complex coacervate of claim 15, wherein the contrast agent comprises tantalum particles, gold particles, or an iodine complex.

17. The adhesive fluid complex coacervate of claim 1, wherein the adhesive fluid complex coacervate further comprises a reinforcing component.

18. The adhesive fluid complex coacervate of claim 17, wherein the reinforcing component comprises natural or synthetic fibers, water-insoluble filler particles, nanoparticles, or microparticles.

19. The adhesive fluid complex coacervate of claim 1, wherein the adhesive fluid coacervate further comprises one or more bioactive agents.

20. The adhesive fluid complex coacervate of claim 19, wherein the bioactive agent comprises an antibiotic, a pain reliever, an immune modulator, a growth factor, an enzyme inhibitor, a hormone, a mediator, a messenger molecule, a cell signaling molecule, a receptor agonist, an oncolytic virus, a chemotherapy agent, a receptor antagonist, a nucleic acid, or any combination thereof.

21. The adhesive fluid complex coacervate of claim 1, wherein the polycation is a synthetic polyguanidino polymer comprising the polymerization product between a monomer selected from the group consisting of an acrylate, a methacrylate, an acrylamide, a methacrylamide, or any combination thereof and a compound of formula I

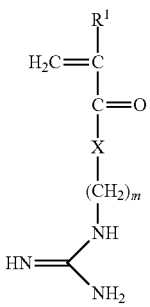

I wherein $R^1$ is hydrogen or an alkyl group, X is oxygen or $NR^5$, where $R^5$ is hydrogen or an alkyl group, and m is 3, or the pharmaceutically-acceptable salt thereof, the polyanion comprises sodium hexametaphosphate, the total positive/negative charge ratio of the polycation solution to the polyanion is from 0.95 to 1.10 and the concentration of NaCl in the adhesive fluid complex coacervate is from 0.5 M to 2.0 M.

22. The adhesive fluid complex coacervate of claim 21, wherein the compound of formula I is an HCl salt.

23. The adhesive fluid complex coacervate of claim 1, wherein the application site is within a blood vessel.

24. An adhesive fluid complex coacervate comprising water, at least one polycation, at least one polyanion, and a salt that produces monovalent ions in water, wherein the salt is sodium chloride, and wherein the concentration of the monovalent ions in the adhesive fluid complex coacervate is greater than the concentration of the monovalent ions present at an application site, and wherein the polyanion comprises a hexametaphosphate salt.

25. The adhesive fluid complex coacervate of claim 24, wherein the concentration of the monovalent ions in the complex coacervate is 1.5 to 10 times greater than the concentration of the monovalent ions at the application site.

26. The adhesive fluid complex coacervate of claim 24, wherein the total positive/negative charge ratio of the polycation to the polyanion is from 4 to 0.25 and the concentration of the monovalent ions in the complex coacervate is from 0.5 M to 2.0 M.

27. The adhesive fluid complex coacervate of claim 24, wherein the adhesive fluid complex coacervate has a pH of 6 to 9.

28. The adhesive fluid complex coacervate of claim 24, wherein the polycation comprises a polyamino compound, wherein the polyamino compound comprises a natural polymer or a synthetic polymer having two or more guanidinyl sidechains.

29. The adhesive fluid complex coacervate of claim 24, wherein the polycation comprises a polyacrylate comprising two or more pendant amino groups.

30. The adhesive fluid complex coacervate of claim 29, wherein the amino group comprises an alkylamino group, a heteroaryl group, a guanidinyl group, an imidazole, or an aromatic group substituted with one or more amino groups, a primary amino group, a secondary amino group, tertiary amino group, or a quaternary amine.

31. The adhesive fluid complex coacervate of claim 24, wherein the polycation is a synthetic polyguanidinyl polymer comprising a copolymer of a monomer selected from the group consisting of an acrylate, a methacrylate, an acrylamide, a methacrylamide, or any combination thereof and a compound of formula I

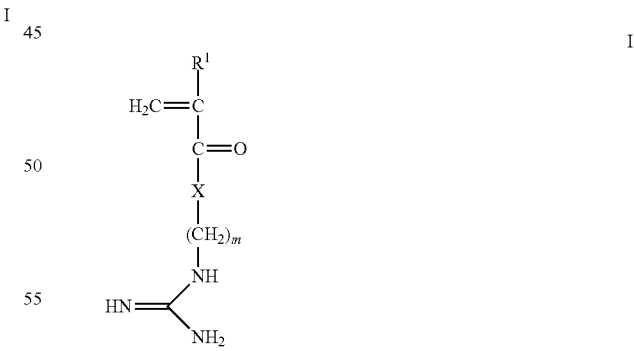

wherein $R^1$ is hydrogen or an alkyl group, X is oxygen or $NR^5$, where $R^5$ is hydrogen or an alkyl group, and m is from 1 to 10, or the pharmaceutically-acceptable salt thereof.

32. The adhesive fluid complex coacervate of claim 31, wherein the polycation comprises polymerization product between the compound of formula I and methacrylamide.

33. The adhesive fluid complex coacervate of claim 31, wherein $R^1$ is methyl, X is NH, m is 3.

34. The adhesive fluid complex coacervate of claim 24, wherein the adhesive fluid complex coacervate further comprises a contrast agent or a visualization agent.

35. The adhesive fluid complex coacervate of claim 34, wherein the contrast agent comprises tantalum particles, gold particles, or an iodine complex.

36. The adhesive fluid complex coacervate of claim 24, wherein the adhesive fluid complex coacervate further comprises a reinforcing component.

37. The adhesive fluid complex coacervate of claim 36, wherein the reinforcing component comprises natural or synthetic fibers, water-insoluble filler particles, nanoparticles, or microparticles.

38. The adhesive fluid complex coacervate of claim 24, wherein the adhesive fluid coacervate further comprises one or more bioactive agents.

39. The adhesive fluid complex coacervate of claim 38, wherein the bioactive agent comprises an antibiotic, a pain reliever, an immune modulator, a growth factor, an enzyme inhibitor, a hormone, a mediator, a messenger molecule, a cell signaling molecule, a receptor agonist, an oncolytic virus, a chemotherapy agent, a receptor antagonist, a nucleic acid, or any combination thereof.

40. The adhesive fluid complex coacervate of claim 24, wherein the polycation is a synthetic polyguanidino polymer comprising the polymerization product between a monomer selected from the group consisting of an acrylate, a methacrylate, an acrylamide, a methacrylamide, or any combination thereof and a compound of formula I

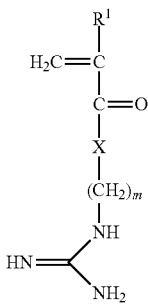

I wherein $R^1$ is hydrogen or an alkyl group, X is oxygen or $NR^5$, where $R^5$ is hydrogen or an alkyl group, and m is 3, or the pharmaceutically-acceptable salt thereof, the polyanion comprises sodium hexametaphosphate, the total positive/negative charge ratio of the polycation solution to the polyanion is from 0.95 to 1.10 and the concentration of NaCl in the adhesive fluid complex coacervate is from 0.5 M to 2.0 M.

41. The adhesive fluid complex coacervate of claim 40, wherein the compound of formula I is an HCl salt.

42. The adhesive fluid complex coacervate of claim 24, wherein the application site is within a blood vessel.

* * * * *

SEQUENCE LISTING

<160> NUMBER OF SEQ ID NOS: 18

<210> SEQ ID NO 1
<211> LENGTH: 191
<212> TYPE: PRT
<213> ORGANISM: Phragmatopoma californica

<400> SEQUENCE: 1

```
Met Lys Val Phe Ile Val Leu Ala Leu Val Ser Ala Ala Tyr Gly Cys
1               5                   10                  15

Gly Val Gly Ile Gly Cys Ala Gly Gly Arg Cys Gly Gly Ala Cys Gly
            20                  25                  30

Gly Lys Gly Tyr Gly Tyr Gly Gly Lys Leu Gly Tyr Gly Ala Tyr Gly
        35                  40                  45

Lys Gly Gly Ile Gly Gly Tyr Gly Tyr Gly Lys Gly Cys Val Gly Gly
    50                  55                  60

Tyr Gly Tyr Gly Gly Leu Gly Ala Gly Lys Leu Gly Tyr Gly Tyr
65                  70                  75                  80

Gly Gly Ser Lys Cys Gly Gly Tyr Gly Tyr Gly Gly Gln Lys Leu Gly
                85                  90                  95

Gly Tyr Gly Tyr Gly Gly Lys Lys Leu Gly Gly Tyr Gly Tyr Ala Ala
            100                 105                 110

Lys Lys Val Gly Gly Tyr Gly Tyr Gly Ala Lys Lys Val Gly Gly Tyr
        115                 120                 125

Gly Tyr Gly Ala Lys Lys Val Gly Gly Tyr Gly Tyr Gly Ala Lys Lys
    130                 135                 140

Val Gly Gly Tyr Gly Tyr Gly Ala Lys Lys Val Gly Gly Tyr Gly Tyr
145                 150                 155                 160

Gly Ala Lys Lys Val Gly Gly Tyr Gly Tyr Gly Ala Lys Lys Val Gly
                165                 170                 175

Gly Tyr Gly Tyr Gly Val Lys Lys Val Gly Gly Tyr Gly Tyr Gly
            180                 185                 190
```

<210> SEQ ID NO 2
<211> LENGTH: 210
<212> TYPE: PRT
<213> ORGANISM: Phragmatopoma californica

<400> SEQUENCE: 2

```
Met Lys Val Leu Ile Phe Leu Ala Thr Val Ala Ala Val Tyr Gly Cys
1               5                   10                  15

Gly Gly Ala Gly Gly Trp Arg Ser Gly Ser Cys Gly Gly Arg Trp Gly
            20                  25                  30

His Pro Ala Val His Lys Ala Leu Gly Gly Tyr Gly Gly Tyr Gly Ala
        35                  40                  45

His Pro Ala Val His Ala Ala Val His Lys Ala Leu Gly Gly Tyr Gly
    50                  55                  60

Ala Gly Ala Tyr Gly Ala Gly Ala Trp Gly His Pro Ala Val His Lys
65                  70                  75                  80

Ala Leu Gly Gly Tyr Gly Ala Gly Ala Trp Gly His Pro Ala Val His
                85                  90                  95

Lys Ala Leu Gly Gly Tyr Gly Tyr Gly Ala His Pro Ala Val His
            100                 105                 110

Val Ala Val His Lys Ala Leu Gly Gly Tyr Gly Ala Gly Ala Cys Gly
        115                 120                 125

His Lys Thr Gly Gly Tyr Gly Gly Tyr Gly Ala His Pro Val Ala Val
```

```
            130                 135                 140
Lys Ala Ala Tyr Asn His Gly Phe Asn Tyr Gly Ala Asn Asn Ala Ile
145                 150                 155                 160

Lys Ser Thr Lys Arg Phe Gly Gly Tyr Gly Ala His Pro Val Val Lys
                165                 170                 175

Lys Ala Phe Ser Arg Gly Leu Ser His Gly Ala Tyr Ala Gly Ser Lys
            180                 185                 190

Ala Ala Thr Gly Tyr Gly Tyr Gly Ser Gly Lys Ala Ala Gly Gly Tyr
            195                 200                 205

Gly Tyr
    210

<210> SEQ ID NO 3
<211> LENGTH: 272
<212> TYPE: PRT
<213> ORGANISM: Phragmatopoma californica

<400> SEQUENCE: 3

Met Pro Thr Leu Tyr Lys Lys Val Gly Lys Leu Val Ile Leu Ala Ile
1               5                   10                  15

Ile Val Thr Val Ala Ser Val Ala Ser Ala Gly Tyr Pro Thr Tyr Ser
            20                  25                  30

Pro Ser Gly Gly Thr His Ser Gly Tyr Asn Gly Pro His Gly Asn Val
        35                  40                  45

Val Lys Lys Thr Tyr Arg Gly Pro Tyr Gly Ala Gly Ala Ala Lys Ala
    50                  55                  60

Trp Asn Gly Tyr His Gly Ala Gly Tyr Thr Ser Val His His Gly Pro
65                  70                  75                  80

Ala Ser Thr Ser Trp His Thr Ser Trp Ser Asn Lys Lys Gly Gly Tyr
                85                  90                  95

Gly Tyr Gly Leu Lys Asn Lys Gly Tyr Gly Tyr Gly Leu Lys Lys Val
            100                 105                 110

Gly Tyr Gly Val Gly Leu His Ala Ala Gly Trp His Gly Val Gly Pro
        115                 120                 125

Tyr Gly Ala Gly Tyr His Gly Ala Gly Trp Asn Gly Leu Gly Tyr His
    130                 135                 140

Gly Ala Gly Tyr Gly Val His Gly Val Gly Leu His Gly Ala Gly Tyr
145                 150                 155                 160

Gly Leu His Gly Val Gly Leu His Gly Val Gly Tyr Gly Leu His Gly
                165                 170                 175

Val Gly Leu His Gly Ala Gly Tyr Gly Leu His Gly Val Gly Leu His
            180                 185                 190

Gly Ala Gly Tyr Gly Ile His Gly Val Gly Leu His Gly Ala Gly Tyr
        195                 200                 205

Gly Ile His Gly Val Gly Leu His Gly Val Gly Tyr Gly Leu His Gly
    210                 215                 220

Val Gly Leu His Gly Ala Gly Tyr Gly Leu His Gly Val Gly Leu His
225                 230                 235                 240

Gly Ala Gly Tyr Gly Ile His Gly Val Gly Leu His Gly Ala Gly Cys
                245                 250                 255

Gly Ile His Lys Thr Ala Cys Tyr Gly Val Gly Leu His Gly His Tyr
            260                 265                 270

<210> SEQ ID NO 4
<211> LENGTH: 144
```

```
<212> TYPE: PRT
<213> ORGANISM: Phragmatopoma californica

<400> SEQUENCE: 4

Met Lys Phe Leu Val Leu Leu Ala Leu Val Ala Ser Ala Ser Ala Tyr
1               5                   10                  15

Tyr Pro Leu Met Gly Gly Phe His Gly Gly Trp His Ala Pro Met Val
                20                  25                  30

His Gly Gly Leu Tyr His Gly Gly Trp His Ala Pro Met Val His Gly
            35                  40                  45

Gly Leu Tyr His Gly Gly Trp His Ala Pro Ile Val His Gly Gly Trp
        50                  55                  60

His Ala Pro Val Phe His Ala Pro Ala Pro Ile His Thr Val Ser His
65                  70                  75                  80

Ser Val Val Asn His Val Pro Met Met Pro Met Trp His His Pro Ala
                85                  90                  95

Pro Ala Pro Ala Pro Ala Pro Arg Pro Gly Arg Thr Ile Ile Leu Gly
                100                 105                 110

Gly Gly Lys Tyr Gly Pro Phe Gly Lys Tyr Gly Gly Ala Gly Leu
            115                 120                 125

Leu Ala Leu Gly Ala Leu Gly Gly Asn Gly Gly Phe Trp Lys Arg Arg
130                 135                 140

<210> SEQ ID NO 5
<211> LENGTH: 328
<212> TYPE: PRT
<213> ORGANISM: Phragmatopoma californica

<400> SEQUENCE: 5

Met Leu Phe Tyr Asn Ala Asn Phe Val Gln Lys Ser Trp Val Leu Ile
1               5                   10                  15

Leu Leu Gly Leu Ala Ala Val Val Ala Cys Ser Glu Tyr Asp Lys Gly
                20                  25                  30

Leu Gly Gly Tyr Gly Arg Pro Ser Tyr Gly Gly Arg Arg Gly Tyr Gly
            35                  40                  45

Gly Arg Arg Gly Leu Gln Tyr His Gly Lys Tyr Gln Gly Arg Cys Glu
        50                  55                  60

Tyr Asp Gly Leu Tyr Phe Arg Asp Glu Lys Ser Phe Val Tyr Cys Ser
65                  70                  75                  80

Asn Arg Asn Ser Tyr Ile Gln Pro Cys Ala Pro Gly Thr Arg Asn Ser
                85                  90                  95

Pro Tyr Thr Lys Tyr Asn Arg Gly Ser Lys Tyr Asn Tyr Arg Asp Phe
                100                 105                 110

Cys Glu Val Asn Leu Val Asp Ser Gly Tyr Val Pro Lys Pro Gly Tyr
                115                 120                 125

Leu Pro Ala Pro Lys Lys Ala Tyr Pro Thr Lys Val Tyr Asp Leu Lys
130                 135                 140

Val Asp Tyr Ala Pro Lys Val Asp Ala Pro Lys Val Asp Tyr Ala
145                 150                 155                 160

Pro Lys Val Asp Tyr Ala Pro Lys Val Asp Tyr Val Ala Pro Lys Ala
                165                 170                 175

Ser Tyr Val Pro Pro Lys Ala Ser Tyr Val Asp Pro Thr Pro Thr Tyr
                180                 185                 190

Gly Tyr Glu Ala Pro Phe Lys Gly Gly Tyr Asp Lys Pro Ser Tyr Gly
                195                 200                 205
```

```
Lys Asp Val Asp Thr Ser Tyr Glu Ser Lys Thr Thr Tyr Thr Val Glu
    210                 215                 220

Lys Thr Ala Asp Lys Gly Tyr Gly Lys Gly Tyr Gly Asp Lys Glu Ile
225                 230                 235                 240

Ser Ala Lys Lys Ser Tyr Thr Leu Thr Glu Lys Arg Asp Tyr Asp Thr
                245                 250                 255

Gly Tyr Asp Asn Ser Arg Ser Asp Glu Asp Ser Lys Glu Tyr Gly Tyr
            260                 265                 270

Asp Asn Asp Arg Ser Glu Ser Tyr Glu Arg Thr Glu Ser Tyr Thr Asp
        275                 280                 285

Glu Arg Thr Asp Gly Tyr Gly Thr Gln Lys Val Glu Tyr Thr Gln Gln
    290                 295                 300

Ser Glu Tyr Asp Arg Val Thr Arg Arg Gly Ile Trp Leu His Lys Gly
305                 310                 315                 320

Thr Glu Val Glu His Val Leu Tyr
                325

<210> SEQ ID NO 6
<211> LENGTH: 136
<212> TYPE: PRT
<213> ORGANISM: Phragmatopoma californica
<220> FEATURE:
<221> NAME/KEY: misc_feature
<222> LOCATION: (49)..(49)
<223> OTHER INFORMATION: Xaa can be any naturally occurring amino acid

<400> SEQUENCE: 6

Met Asn Thr Phe Val Val Leu Ala Ala Ile Val Ala Val Ala Ala Cys
1               5                   10                  15

Ser Gly Gly Tyr Asp Gly Arg Gln Tyr Thr Tyr Arg Gly Arg Tyr Asn
            20                  25                  30

Asn Lys Cys Gly Asn Asp Gly Leu Tyr Phe Lys Asp Asp Lys Asn Phe
        35                  40                  45

Xaa Phe Cys Ser Asn Gly Asn Ser Tyr Val Gln Pro Cys Ala Pro Gly
    50                  55                  60

Thr Arg Asn Ser Gly Tyr Asn Asn Tyr Lys Gln Gly Ser Ile Tyr Asn
65                  70                  75                  80

Tyr Arg Asp Phe Cys Asp Val Asn Leu Val Asp Glu Gly Tyr Gly Val
                85                  90                  95

Gly Ala Lys Pro Gly Tyr Asn Lys Gly Tyr Asn Pro Gly Tyr Asn Pro
            100                 105                 110

Gly Tyr Gly Gly Tyr Asn Pro Gly Tyr Ser Thr Gly Tyr Gly Gly Tyr
        115                 120                 125

Lys Ala Gly Pro Gly Pro Tyr Trp
    130                 135

<210> SEQ ID NO 7
<211> LENGTH: 158
<212> TYPE: PRT
<213> ORGANISM: Phragmatopoma californica

<400> SEQUENCE: 7

Met Lys Leu Ala Leu Leu Leu Val Ala Val Cys Ala Ala Val Ala
1               5                   10                  15

Val Asn Ala Cys Gly Pro Leu Gly Cys Ser Gly Gly Tyr Gly Gly Val
            20                  25                  30

Leu Lys Cys Gly Val Gly Gly Cys Ala Leu Gly Gly Tyr Gly Gly Gly
        35                  40                  45
```

Tyr Ser Ala Gly Ile Gly Gly Tyr Gly Ile Lys Arg Leu Gly Cys Arg
            50                  55                  60

Gly Gly Arg Cys Gly Leu Arg Arg Val Gly Cys Arg Gly Gly Arg
65                  70                  75                  80

Cys Gly Leu Arg Gly Arg Leu Gly Cys Arg Gly Arg Cys Gly Leu
                85                  90                  95

Arg Lys Leu Gly Cys Arg Gly Gly Arg Cys Gly Leu Arg Gly Arg Leu
            100                 105                 110

Gly Cys Arg Gly Gly Arg Cys Gly Leu Arg Lys Arg Leu Gly Cys Arg
            115                 120                 125

Gly Gly Arg Cys Gly Arg Gly Tyr Gly Gly Tyr Gly Val
            130                 135                 140

Cys Ser Lys Gly Val Cys Gly Gly Tyr Pro Ala Tyr Gly Lys
145                 150                 155

<210> SEQ ID NO 8
<211> LENGTH: 236
<212> TYPE: PRT
<213> ORGANISM: Phragmatopoma californica

<400> SEQUENCE: 8

Met Lys Val Ser Ile Ala Val Leu Ile Met Cys Cys Ile Ala Ala Val
1               5                   10                  15

Leu Ala Asp Gly Tyr Lys Ser Lys Asn Gly Gly Gln Ala Gly Gly Tyr
            20                  25                  30

Gly Gly Tyr Gly Ser Gly Tyr Gly Gly Gly Tyr Gly Gly Gly Tyr Asp
            35                  40                  45

Gly Gly Tyr Gly Gly Glu Lys Gly Lys Ser Lys Gly Tyr Gly Asp
50                  55                  60

Arg Lys Gly Lys Ser Glu Lys Gly Tyr Gly Asn Gly Lys Lys Gly
65                  70                  75                  80

Gly Ser Gly Tyr Gly Gly Gly Tyr Asp Gly Gly Tyr Gly Gly Lys
            85                  90                  95

Gly Lys Ser Gly Ser Gly Tyr Gly Gly Gly Tyr Asp Gly Gly Tyr Gly
            100                 105                 110

Gly Gly Lys Gly Lys Ser Gly Ser Gly Tyr Gly Gly Gly Tyr Asp Gly
            115                 120                 125

Gly Tyr Asp Gly Gly Tyr Gly Gly Gly Lys Gly Lys Ser Gly Ser Gly
            130                 135                 140

Phe Gly Gly Gly Tyr Asp Gly Gly Tyr Asp Gly Gly Tyr Gly Gly Gly
145                 150                 155                 160

Lys Gly Lys Ser Gly Ser Gly Tyr Gly Gly Gly Tyr Asp Gly Gly Tyr
                165                 170                 175

Asp Gly Gly Tyr Gly Gly Gly Lys Gly Lys Ser Gly Ser Gly Tyr Gly
            180                 185                 190

Gly Gly Tyr Asp Gly Gly Tyr Asp Gly Gly Tyr Gly Gly Gly Lys Gly
            195                 200                 205

Lys Ser Gly Ser Gly Tyr Gly Gly Gly Tyr Asp Gly Gly Tyr Asp Gly
            210                 215                 220

Arg Tyr Gly Gly Gly Lys Gly Lys Ser Gly Ser Gly
225                 230                 235

<210> SEQ ID NO 9
<211> LENGTH: 191
<212> TYPE: PRT

<213> ORGANISM: Phragmatopoma californica

<400> SEQUENCE: 9

Met Lys Leu Ile Cys Leu Val Leu Leu Ala Val Cys Ile Val Ala Val
1               5                   10                  15

Ser Ala Ser Ser Ser Gly Gly Arg Arg Arg Val Ile Val Ile
            20                  25                  30

Gly Asn Arg Gly Arg Ala Pro Ala Arg Pro Arg Ser Asn Ile His Tyr
            35                  40                  45

His Met His Ala Pro Gln Pro Arg Met Met Met Ala Pro Arg Met Met
        50                  55                  60

Met Ala Pro Met Met Met Ala Pro Met Ala Met Pro Ala Thr Ser His
65                  70                  75                  80

Val Tyr Gln Ser Val Ser Tyr Pro Gly Ala Met Tyr Arg Tyr Gly Leu
                85                  90                  95

Gly Ser Leu Gly Gly Gly Phe Ile Ser Gly Gly Leu Gly Gly Ile Val
            100                 105                 110

Gly Gly Gly Leu His Gly Gly Val Val Thr Ser Gly Leu His Gly Gly
            115                 120                 125

Val Val Thr Ser Gly Leu His Gly Gly Val Val Thr Ser Gly Leu His
    130                 135                 140

Gly Gly Leu Val Ser Gly Gly Trp His Ser Gly Val Val Ser His Gly
145                 150                 155                 160

Gly Leu Ile Gly Gly Gly Ile His Thr Thr Tyr Gly Gly Phe His Lys
                165                 170                 175

Gly Val Val His Gly Gly Tyr Thr Gly His Tyr Gly Lys Arg Arg
            180                 185                 190

<210> SEQ ID NO 10
<211> LENGTH: 102
<212> TYPE: PRT
<213> ORGANISM: Phragmatopoma californica

<400> SEQUENCE: 10

Met Lys Leu Ala Val Phe Ala Leu Leu Val Ala Phe Ala Ile Val Tyr
1               5                   10                  15

Thr Ala Glu Gly Leu Val Tyr Gly Gly Gln Lys Gly Tyr Gly Tyr Gly
            20                  25                  30

Gly Lys Gly Tyr Gly Tyr Gly Cys Thr Gly Gly Tyr Gly Leu Tyr Gly
            35                  40                  45

Gly Lys Gly Tyr Gly Tyr Gly Lys Gly Tyr Gly Tyr Gly Cys Arg Gly
        50                  55                  60

Gly Tyr Gly Tyr Gly Lys Gly Tyr Gly Tyr Gly Lys Tyr Arg Gly
65                  70                  75                  80

Tyr Gly Tyr Gly Asn Lys Val Gly Tyr Gly Tyr Gln Gln Leu Gly
                85                  90                  95

Tyr Lys Asn Gly Arg Lys
            100

<210> SEQ ID NO 11
<211> LENGTH: 91
<212> TYPE: PRT
<213> ORGANISM: Phragmatopoma californica

<400> SEQUENCE: 11

Leu Asp Gly Gly Cys Lys Pro Thr Gly Gly Phe Ile Lys Gly Ser Val
1               5                   10                  15

-continued

Gly Pro Cys Gly Gly Tyr Asn His Gln His Val Val Gly Pro Asn Gly
                20                  25                  30

Ala His Gly Arg Arg Val Gly Tyr Gly Pro Asn Gly Lys Tyr Ser Gln
            35                  40                  45

Ile Tyr Gly Asn Gly Pro Gly Gly Arg Tyr Ser His Thr Val Val Tyr
50                  55                  60

Pro Arg Val Arg Pro Tyr Gly Tyr Gly Phe Lys Gly Gly Tyr Gly
65                  70                  75                  80

Gly Tyr His Gly Val Gly Tyr Lys Gly Tyr
                85                  90

<210> SEQ ID NO 12
<211> LENGTH: 145
<212> TYPE: PRT
<213> ORGANISM: Phragmatopoma californica

<400> SEQUENCE: 12

Met Lys Val Phe Val Ala Ala Leu Leu Leu Cys Cys Ile Ala Ala Ala
1               5                   10                  15

Ala Ala Glu Asp Gly Tyr Gly Phe Gly Tyr Asp Gly Tyr Gly Ser Gly
                20                  25                  30

Tyr Gly Tyr Asp Gly Tyr Ser Tyr Gly Gly Asp Lys Gly Tyr Gly Tyr
            35                  40                  45

Gly Lys Gly Lys Gly Tyr Gly Tyr Glu Gly Gly Lys Gly Tyr Gly Tyr
50                  55                  60

Glu Gly Gly Lys Gly Tyr Gly His Glu Glu Gly Lys Gly Tyr Gly His
65                  70                  75                  80

Glu Gly Gly Lys Gly Tyr Gly Tyr Glu Gly Gly Lys Gly Tyr Gly Tyr
                85                  90                  95

Gly Gly Gly Lys Gly Tyr Gly His Asp Gly Gly Lys Gly Tyr Gly His
                100                 105                 110

Asp Gly Gly Lys Gly Tyr Gly Tyr Gly Gly Lys Gly Tyr Gly His
            115                 120                 125

Glu Gly Gly Lys Gly Tyr Gly Tyr Glu Gly Gly Lys Gly Tyr Gly Lys
    130                 135                 140

Tyr
145

<210> SEQ ID NO 13
<211> LENGTH: 134
<212> TYPE: PRT
<213> ORGANISM: Phragmatopoma californica

<400> SEQUENCE: 13

Met Arg Ile Val Ile Cys Leu Leu Val Leu Val Ala Gly Ala Tyr Gly
1               5                   10                  15

Ile Gly Cys Gly Tyr Gly Gly Tyr Gly Gly Tyr Gly Gly Gly Phe His
                20                  25                  30

Gly Gly Tyr Ile Gly Tyr His Gly Gly Tyr Pro Gly Tyr Ser Gly Gly
            35                  40                  45

Phe Arg Gly Tyr Gly Tyr Pro Gly Arg Val His Thr Asn Val Val His
50                  55                  60

His Asn Ile Pro Val Phe Met Pro Pro Met Pro Arg Arg Ala Pro
65                  70                  75                  80

Ala Pro Ala Pro Arg Gly Arg Thr Ile Ile Leu Gly Gly Gly Lys Tyr
                85                  90                  95

```
Gly Leu Phe Gly Lys Ser Lys Asn Lys Gly Phe Gly Gly Leu Gly
                100                 105                 110

Val Leu Ser Leu Leu Gly Gly Leu Gly Lys Gly Gly Gly Ile
            115                 120                 125

Arg Phe Leu Gly Arg Lys
        130
```

<210> SEQ ID NO 14
<211> LENGTH: 226
<212> TYPE: PRT
<213> ORGANISM: Phragmatopoma californica

<400> SEQUENCE: 14

```
Met Lys Val Ile Ile Leu Leu Ala Thr Val Ala Ala Val Tyr Gly Cys
1               5                   10                  15

Gly Gly Trp Asn Gly Gly Phe Gly Gly Lys Ala Cys Gly Gly Gly
            20                  25                  30

Trp Gly Ala Lys Ala Leu Gly Gly Tyr Gly Ser Tyr Asn Gly Asn Gly
        35                  40                  45

Tyr Gly Ala His Pro Val Ala Val Lys Ser Ala Phe Asn Lys Gly Val
50                  55                  60

Ser Tyr Gly Ala Arg Ser Ala Val Lys Ala Thr Arg Gly Phe Ala Tyr
65                  70                  75                  80

Gly Lys Gly Ser Ser Tyr Gly Tyr Gly Ala His Pro Ala Val Lys Ser
                85                  90                  95

Ala Phe Gly Asn Gly Phe Lys Thr Gly Ala His Ala Ala Val Asn Gly
            100                 105                 110

Tyr Gly Tyr Gly Ala Val Lys Ser Ala Leu Ser Gly Tyr Gly Tyr
        115                 120                 125

Gly Ser Tyr Gly Ala His Pro Ala Val Lys Ser Ala Tyr Arg Lys Gly
    130                 135                 140

Leu Ser Tyr Gly Ala Lys Ser Ala Val Lys Ala Thr Arg Gly Phe Ala
145                 150                 155                 160

Tyr Gly Arg Ser Gly Tyr Gly Ala His Pro Val Val Lys Ser Ala Phe
                165                 170                 175

Ser Asn Gly Phe Lys Tyr Gly Ala His Ala Ala Val Lys Ala Thr Asn
            180                 185                 190

Gly Tyr Gly Tyr Gly Ala Val His Pro Ala Val Lys Ala Ala Val Lys
        195                 200                 205

Gly Gly Tyr Gly Tyr Gly Asn Lys Gly Tyr Gly Ala Gly Tyr Ala
    210                 215                 220

Ala Tyr
225
```

<210> SEQ ID NO 15
<211> LENGTH: 89
<212> TYPE: PRT
<213> ORGANISM: Phragmatopoma californica

<400> SEQUENCE: 15

```
Met Lys Val Phe Val Ala Thr Leu Leu Leu Cys Cys Ile Ala Ala Ala
1               5                   10                  15

Ala Ala Ala Gly Tyr Gly Asn Gly Tyr Ala Gly Tyr Gly Ser Gly Tyr
            20                  25                  30

Ala Gly Tyr Gly Thr Gly Tyr Ala Gly Tyr Gly Ser Gly Tyr Gly Tyr
        35                  40                  45
```

```
Asp Gly Tyr Gly Tyr Gly Gly Lys Gly Tyr Gly Tyr Gly Gly Asp
    50                  55                  60

Lys Gly Tyr Gly Tyr Gly Gly Lys Gly Tyr Gly Tyr Gly Gly Gln Lys
65                  70                  75                  80

Gly Tyr Gly Tyr Gly Tyr Gly Lys Tyr
                85

<210> SEQ ID NO 16
<211> LENGTH: 105
<212> TYPE: PRT
<213> ORGANISM: Phragmatopoma californica

<400> SEQUENCE: 16

Met Lys Leu Leu Leu Phe Ala Leu Ala Ala Val Ala Val Ala Leu
1               5                   10                  15

Pro Tyr Gly Tyr Ser Gly Lys Pro Gly Tyr Gly Tyr Asp Ala Val Asp
                20                  25                  30

Ala Val Tyr Asn Arg Leu Ala Asp Lys Gln Gln Ala Val Asn Arg Lys
            35                  40                  45

Ala Glu Tyr Val Gly Ala Gly Thr Gly Thr Ala Lys Tyr Asn Gly Val
50                  55                  60

Pro Gly Ala Asn Tyr Gly Tyr Glu Asn Asp Arg Lys Tyr Gly Tyr Asp
65                  70                  75                  80

Asn Lys Gly Tyr Gly Tyr Gly Tyr Gly Asp Lys Gly Tyr Gly Gly Tyr Gly
                85                  90                  95

Asp Lys Gly Leu Tyr Asp Gly Tyr Tyr
            100                 105

<210> SEQ ID NO 17
<211> LENGTH: 275
<212> TYPE: PRT
<213> ORGANISM: Phragmatopoma californica

<400> SEQUENCE: 17

Lys Tyr Tyr Asp Asp Glu Lys Arg Asp Ala Asp Lys Tyr Arg Lys Pro
1               5                   10                  15

Ser Tyr Asn Pro Tyr Asn Thr Tyr Lys Asp Tyr Pro Pro Lys Lys Ile
                20                  25                  30

Tyr Asn Asp Asp Glu Lys Arg Asp Ala Asp Gln Tyr Arg Ile Ser Tyr
            35                  40                  45

Asn Pro Tyr Asn Thr Tyr Lys Asp Tyr Pro Pro Lys Lys Tyr Tyr
50                  55                  60

Asp Asp Glu Lys Arg Asp Ala Tyr Lys Tyr Arg Asn Pro Ser Tyr Asn
65                  70                  75                  80

Pro Tyr Asn Thr Tyr Lys Asp Tyr Pro Pro Lys Lys Ile Tyr Tyr Asp
                85                  90                  95

Asp Glu Lys Arg Asp Ala Asp Gln Tyr Arg Asn Pro Ser Tyr Asn Pro
            100                 105                 110

Tyr Asn Thr Tyr Lys Asp Tyr Pro Pro Lys Lys Tyr Tyr Asp Asp
        115                 120                 125

Glu Lys Arg Asp Ala Asp Gln Tyr Arg Asn Pro Ser Tyr Asn Pro Tyr
130                 135                 140

Asn Thr Tyr Lys Asp Tyr Leu Pro Lys Lys Tyr Tyr Asp Asp Glu
145                 150                 155                 160

Lys Arg Asp Ala Asp Gln Tyr Arg Lys Pro Ser Tyr Asn Pro Tyr Asn
            165                 170                 175
```

```
Ser Tyr Lys Asp Tyr Pro Pro Lys Lys Lys Tyr Tyr Asp Asp Glu Lys
            180                 185                 190

Arg Asp Ala Asp Gln Tyr Arg Asn Pro Ser Tyr Asn Pro Tyr Asn Thr
            195                 200                 205

Tyr Lys Asp Tyr Leu Pro Lys Lys Lys Tyr Tyr Asp Asp Glu Lys Arg
        210                 215                 220

Asp Ala Asp Gln Tyr Arg Asn Pro Ser Tyr Asn Pro Tyr Asn Thr Tyr
225                 230                 235                 240

Lys Asp Tyr Pro Pro Lys Lys Lys Tyr Tyr Asp Asp Glu Lys Arg Asp
                245                 250                 255

Ala Asp Gln Tyr Arg Asn Pro Ser Tyr Asn Pro Tyr Asn Thr Tyr Lys
            260                 265                 270

Asp Tyr Pro
        275

<210> SEQ ID NO 18
<211> LENGTH: 32
<212> TYPE: PRT
<213> ORGANISM: Artificial Sequence
<220> FEATURE:
<223> OTHER INFORMATION: Synthetic Construct

<400> SEQUENCE: 18

Pro Arg Arg Arg Arg Ser Ser Ser Arg Pro Ile Arg Arg Arg Arg Pro
1               5                   10                  15

Arg Arg Ala Ser Arg Arg Arg Arg Arg Gly Gly Arg Arg Arg Arg
            20                  25                  30
```